United States Patent
Chan et al.

(10) Patent No.: US 10,685,461 B1
(45) Date of Patent: Jun. 16, 2020

(54) APPARATUS AND METHOD FOR CONTEXT-ORIENTED ITERATIVE RECONSTRUCTION FOR COMPUTED TOMOGRAPHY (CT)

(71) Applicants: CANON MEDICAL SYSTEMS CORPORATION, Otawara-shi (JP); UNIVERSITY HEALTH NETWORK, Toronto (CA)

(72) Inventors: Chung Chan, Glenview, IL (US); Zhou Yu, Wilmette, IL (US); Jian Zhou, Buffalo Grove, IL (US); Patrik Rogalla, Toronto (CA); Bernice Hoppel, Delafield, WI (US); Kurt Walter Schultz, North Providence, RI (US)

(73) Assignees: CANON MEDICAL SYSTEMS CORPORATION, Otawara-shi (JP); UNIVERSITY HEALTH NETWORK, Toronto (CA)

( * ) Notice: Subject to any disclaimer, the term of this patent is extended or adjusted under 35 U.S.C. 154(b) by 0 days.

(21) Appl. No.: 16/228,512

(22) Filed: Dec. 20, 2018

(51) Int. Cl.
*G06K 9/00* (2006.01)
*G06T 11/00* (2006.01)
(Continued)

(52) U.S. Cl.
CPC ............ *G06T 11/006* (2013.01); *A61B 6/032* (2013.01); *A61B 6/5205* (2013.01);
(Continued)

(58) Field of Classification Search
None
See application file for complete search history.

(56) References Cited

U.S. PATENT DOCUMENTS 9,478,049 B2  10/2016  Bippus et al.
2015/0049930 A1  2/2015  Brown
(Continued)

OTHER PUBLICATIONS

Idris A. Elbakri, et al. "Statistical Image Reconstruction for Polyenergetic X-Ray Computed Tomography", IEEE TMI, vol. 21, No. 2, Feb. 2002.
(Continued)

*Primary Examiner* — Atiba O Fitzpatrick
(74) *Attorney, Agent, or Firm* — Oblon, McClelland, Maier & Neustadt, L.L.P.

(57) ABSTRACT

A method and apparatus is provided to iteratively reconstruct a computed tomography (CT) image using a spatially-varying content-oriented regularization parameter, thereby achieving uniform statistical properties within respective organs/regions and different statistical properties (e.g., degree of smoothing and noise level) among the respective organs/regions. For example, less smoothing and sharper features/resolution can be applied within a lung region than within a soft-tissue region by using a smaller regularization parameter value in the lung region than in the soft-tissue region. This can be achieved, e.g., using a minimum intensity projection to suppress/eliminate sub-solid nodules in the lung region. The content-oriented regularization parameter can be generated by reconstructing an initial CT image, which is then segmented/classified according to organs and/or tissue type. Segmenting the image and generating the content-oriented regularization parameter can be integrated into one process by applying an HU-to-$\beta$ mapping to the CT image.

6 Claims, 19 Drawing Sheets

(51) Int. Cl.
    *G06K 9/62*       (2006.01)
    *G06T 7/11*       (2017.01)
    *G06T 5/00*       (2006.01)
    *A61B 6/03*       (2006.01)
    *A61B 6/00*       (2006.01)
    *G01N 23/046*     (2018.01)

(52) U.S. Cl.
    CPC ............ *G06K 9/6267* (2013.01); *G06T 5/002* (2013.01); *G06T 7/11* (2017.01); *G01N 23/046* (2013.01); *G01N 2223/401* (2013.01); *G06K 2209/05* (2013.01); *G06T 2207/10081* (2013.01); *G06T 2207/30004* (2013.01); *G06T 2211/424* (2013.01)

(56) References Cited

U.S. PATENT DOCUMENTS

| | | | |
|---|---|---|---|
| 2016/0225169 A1* | 8/2016 | Bippus | .................. G06T 11/006 |
| 2017/0178316 A1 | 6/2017 | Simon | |
| 2017/0294034 A1 | 10/2017 | Zhou et al. | |

OTHER PUBLICATIONS

Jeffrey A. Fessler, et al. "Spatial Resolution Properties of Penalized-Likelihood Image Reconstruction: Space-Invariant Tomographs" IEEE Transactions on Image Processing, vol. 5, No. 9, pp. 1346-1358, Sep. 1996.

Stephen M. Schmitt, et al. "Fast Variance Prediction for Iteratively Reconstructed CT Images with Locally Quadratic Regularization", IEEE TMI, Jan. 2017.

\* cited by examiner

Transverse

Coronal

Sagittal

Transverse

Coronal

Sagittal ww/wl: 40/400 ww/wl: 40/400

APPARATUS AND METHOD FOR CONTEXT-ORIENTED ITERATIVE RECONSTRUCTION FOR COMPUTED TOMOGRAPHY (CT)

FIELD

This disclosure relates to iterative reconstruction (IR) for computed tomography (CT) using a spatially-varying regularization parameter (e.g., a multiplicative factor) that scales a regularization term, and, more particularly, to using and organ/region-dependent regularization parameter multiplied by a statistics-based spatially-varying regularization parameter that when applied to the regularization term results in uniform smoothing within respective organs/regions and different degrees of smoothing among the organs/regions based on their content/context.

BACKGROUND

Computed tomography (CT) systems and methods are widely used, particularly for medical imaging and diagnosis. A CT scan can be performed by positioning a patient on a CT scanner in a space between an X-ray source and X-ray detector, and then taking X-ray projection images through the patient at different angles as the X-ray source and detector are rotated through a scan. The resulting projection data is referred to as a CT sinogram, which represents attenuation through the body as a function of position along one or more axis and as a function of projection angle along another axis. Performing an inverse Radon transform—or any other image reconstruction method—on the projection data to reconstruct a tomographic image.

Various methods can be used to reconstruct CT images from projection data, including filtered back-projection (FBP) and statistical iterative reconstruction (IR) algorithms. Compared to FBP reconstruction methods, IR methods can provide improved image quality at reduced radiation doses. Often IR methods include a regularization term (also referred to as a "regularizer") to encourage/constrain/impose a particular aspect or quality in the reconstructed image (e.g., smoothness or piecewise uniformity in the radiodensity). For example, when the regularizer imposes smoothness on the reconstructed image, a regularization parameter $\beta$ determines the degree of smoothing imposed, and the regularization parameter $\beta$ can be spatially-varying to impose different degrees of smoothing at different points within the reconstructed image.

In J. A. Fessler et al., "Spatial Resolution Properties of Penalized-Likelihood Image Reconstruction: Space-Invariant Tomographs," IEEE Transactions on Image Processing, vol. 5, 1346-1358 (1996) and in U.S. Pat. No. 9,478,049, a spatially-varying regularization parameter $\beta$ was proposed to provide either uniform resolution or uniform statistical properties (e.g., signal-to-noise ration SNR) throughout a reconstructed image. However, sometimes images with uniform resolution or with uniform statistical properties do not produce an image with the best qualities for a particular application. Accordingly, improved methods are desired for reconstructing images for particular applications.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1A:
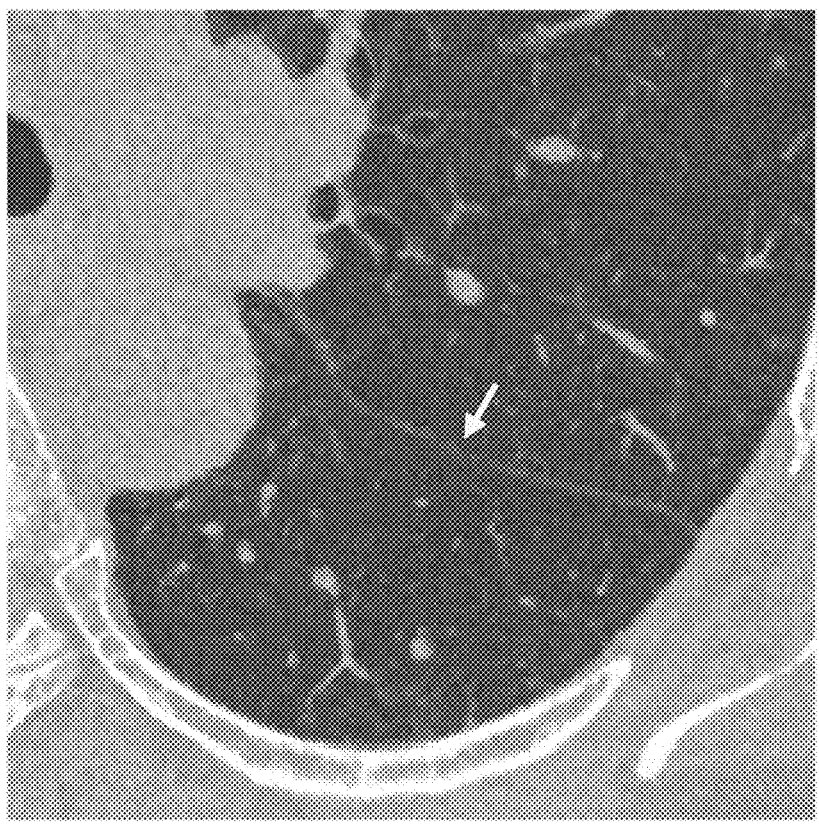
FIG. 1A shows an example of a lung region in slice of a reconstructed computed tomography (CT) image that was generated using a small smoothing/denoising parameter and that is displayed using lung settings (i.e., the window level is WL=−400 Hounsfield Units (HU) and the window width is WW=1500 HU), according to one implementation.

Statistical iterative reconstruction (IR) algorithms are often formulated as an unconstrained (or constrained) optimization problem/search for the argument p (i.e., reconstructed image) that minimize a cost/objective function having a data fidelity term (e.g., $\|A_p - l\|^2$) and a regularizer U(p) that is weighted by a regularization parameter β, i.e., the optimization problem can be expressed as $$\underset{p}{\mathrm{argmin}}\{\|Ap - l\|_W^2 + \beta U(p)\},$$

Various iterative reconstruction (IR) methods exist for conducting the optimization search, such as the algebraic reconstruction methods, expectation-maximization (EM) methods, and maximum likelihood (ML) methods, gradient descent methods, dual-primal methods, Chambolle-Pock algorithms, alternating direction method of multipliers methods, augmented Lagrangian multiplier methods, methods using accelerators (e.g., separable quadratic surrogates and Nesterov acceleration), etc.

The data-fidelity term can be expressed as $\|A_p - l\|^2$, wherein l is the projection data representing the logarithm of the X-ray intensity of projection images taken at a series of projection angles and p is a reconstructed image of the X-ray attenuation for voxels/volume pixels (or two-dimensional pixels in a two-dimensional reconstructed image) in an image space. For the system matrix A, each matrix value $a_{ij}$ (i being a row index and j being a column index) represents an overlap between the volume corresponding to voxel $p_j$ and the X-ray trajectories corresponding to projection value $l_i$. The data-fidelity term $\|A_p - l\|^2$ is minimized when the forward projection A of the reconstructed image p provides a good approximation to all measured projection images l.

In the objective function, the regularization term can be given by a function U(p), which imposes a roughness penalty on the reconstructed image p (i.e., U(p) decreases as the local variance/noise in the reconstructed image decreases). Accordingly, the function U(p) can have the effect of smoothing or denoising the reconstructed image. The value β is a regularization parameter is a value that weights the relative contributions of the data fidelity term and the regularization term. As the regularization parameter β increases the relatively influence of the regularizer on the reconstructed images increases relative to that of the data fidelity, resulting in the reconstructed image having increased smoothing.

In general, a trade-off exists between increase smoothing and better resolution. The value for the regularization parameter β can affect a tradeoff between noise and resolution. In general, increasing the regularization parameter β reduces the noise, but at the cost of also reducing resolution. The best value for the regularization parameter β can depend on multiple factors, including the organ that is being imaged and the application for which the image is being reconstructed.

As discussed above, other methods of choosing the values for a spatially-varying regularization parameter β aim towards either uniform resolution or uniform statistical properties. However, in clinical practice, uniformity throughout the reconstructed image might not be desirable. For example, in some regions/organs better resolution is desirable (e.g., in high-contrast regions such as the lungs where the higher noise level due to less smoothing is still significantly below the signal level), whereas, in other regions/organs, it is better to sacrifice resolution in order to suppress noise (e.g., in low-contrast regions, such as soft tissues, greater smoothing is desired in order to suppress the noise below the signal level).

The methods provided herein generate a spatially-varying regularization parameter β that enables the degree of smoothing to be spatially varied across a reconstructed image to better optimize the tradeoff between reducing noise and increasing resolution. To this end, the values of the regularization parameter β are selected based on the content/context in the image. For example, an initial reconstructed image is classified/segmented into regions/organs, and different degrees of smoothing are assigned based on the different regions/organs.

The best value for the regularization parameter β can vary from organ to organ (or region to region) within a given image. For example, more smoothing might be desired in mostly uniform region, such as a liver, with low contrast features, whereas less smoothing might be better in a region with higher contrast features, such as in the lungs. Accordingly, the methods described herein use a spatially-varying regularization parameter β to locally optimize the tradeoff between resolution and noise based on the particular content/context of a displayed image.

In various implementations, the methods described herein apply an anatomical context-oriented regularized iterative reconstruction (IR) algorithm to produce an image with organ-dependent signal-to-noise ratio (SNR).

In various implementations, the methods described herein produce a trauma-pan scan in a single reconstruction. This achieved by: (i) generating a preliminary reconstructed image; (ii) applying a classification method to generate an organ-dependent β-map based on the preliminary reconstruction; (iii) applying the organ map to scale another spatially-varying regularization parameter β (e.g., a statistically-based regularization parameter $β_s$) to generate the total β-map $β_{Total}$ (e.g., $β_{Total}=β_s>β_c$, wherein is the organ-dependent β-map, also referred to as content-oriented β-map); (iv) using the total β-map in any regularized IR algorithm to generate a reconstructed image having different degrees of uniform smoothing in the respective regions identified in the classification step.

Further, in various implementations, the methods described herein can include that the classification step is performed using, in part, a minimum intensity projection (MIP) method to eliminate sub-solid lung nodules in the lungs for better classification. Additionally, the classification step can include that a hierarchical piece-wise linear HU-to-β mapping is used to generate the organ-dependent β-map.

Figure 1B:
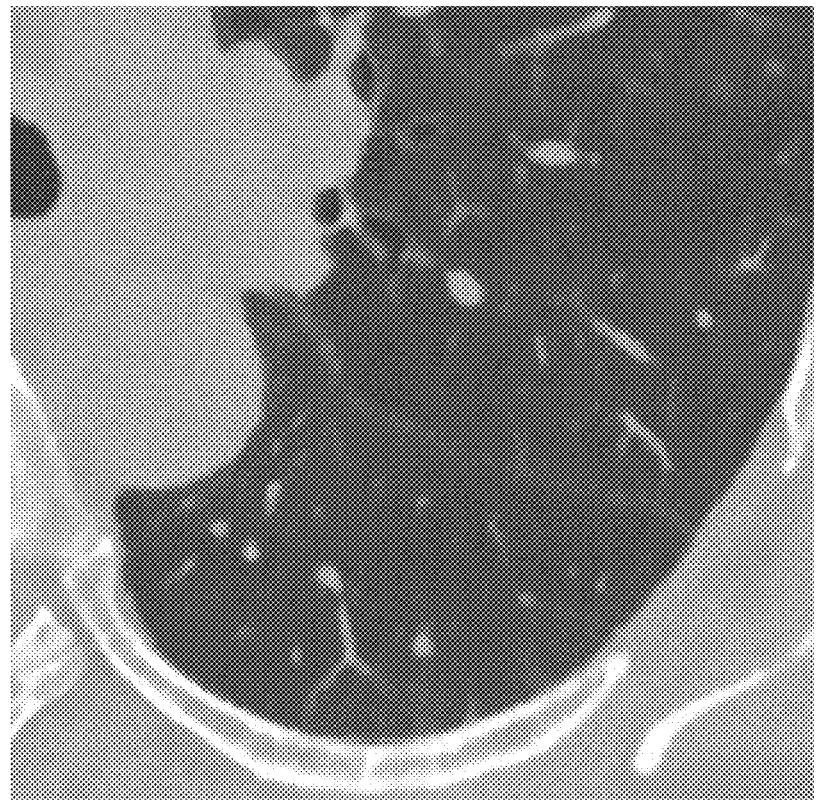
FIG. 1B shows an example of the same lung region using the same display settings as in FIG. 1A, except the CT image was generated using a large smoothing/denoising parameter rather than the small smoothing/denoising parameter used in FIG. 1A, according to one implementation.
Figure 2A:
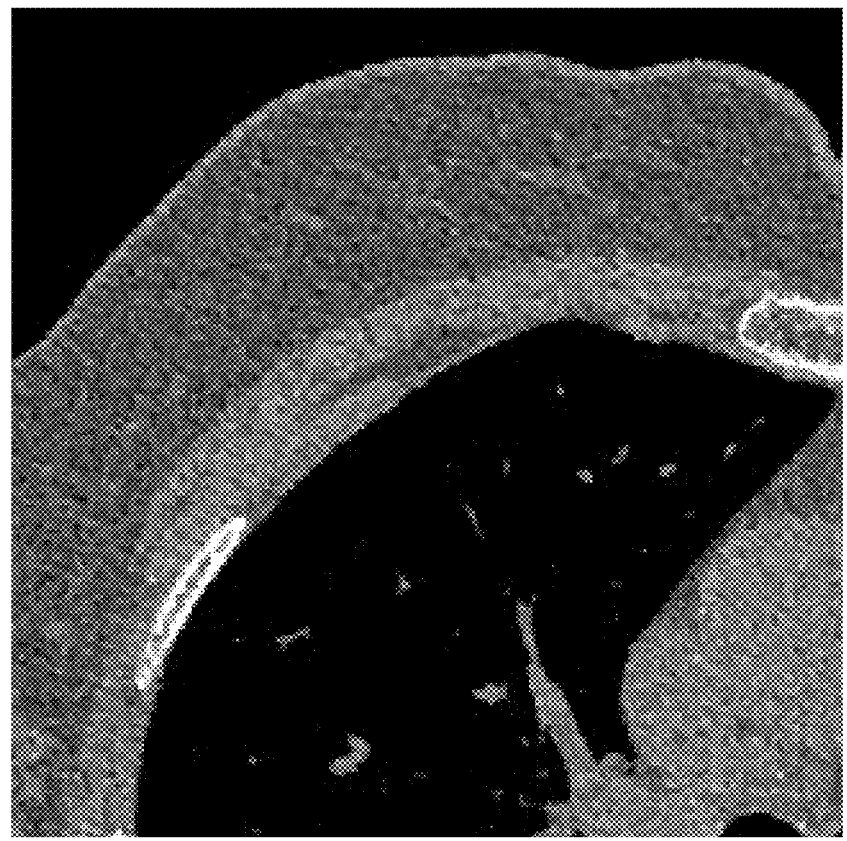
FIG. 2A shows an example of a soft-tissue region in slice of the CT image that was generated using the small smoothing/denoising parameter and the image is displayed using soft-tissue settings (i.e., WL=40 HU and WW=400 HU), according to one implementation.
Figure 2B:
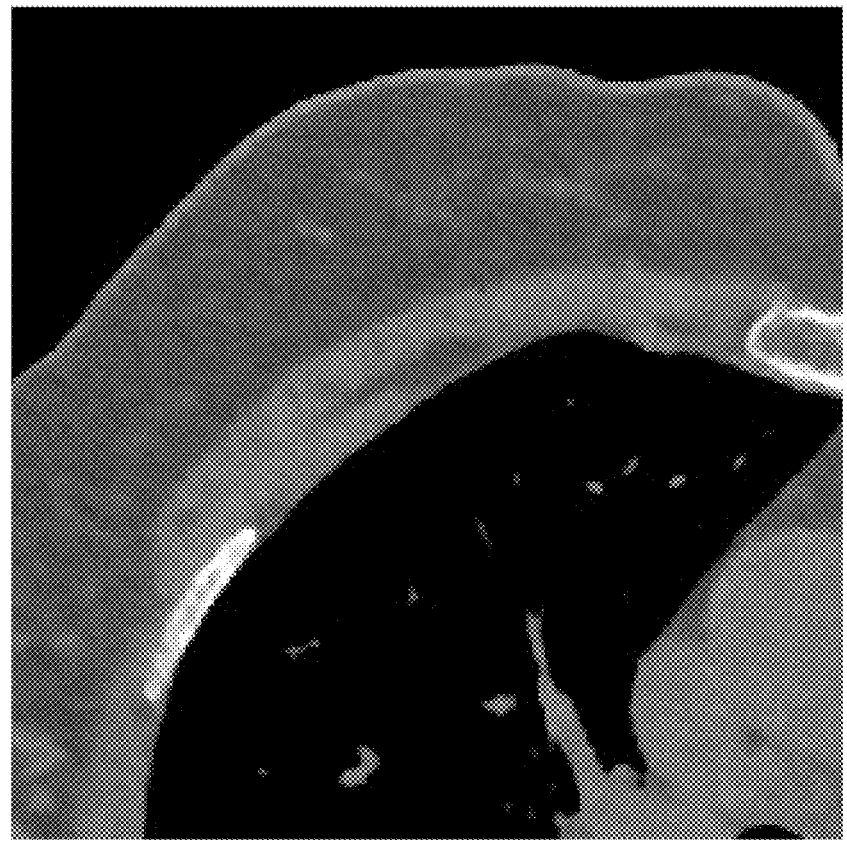
FIG. 2B shows an example of the same soft-tissue region and soft-tissue display settings as in FIG. 2A, except the CT image was generated using the large smoothing/denoising parameter, according to one implementation.

Referring now to the drawings, wherein like reference numerals designate identical or corresponding parts throughout the several views, FIGS. 1A and 1B show respective images of the same lung region but with different degrees of denoising (which herein is interchangeably referred to as smoothing). Similarly, FIGS. 2A and 2B show respective images of the same soft-tissue region with different degrees of denoising. FIGS. 1A and 2A represent a first degree of denoising, and FIGS. 1B and 2B represent a second degree of denoising with more denoising/smoothing than the first degree of denoising shown in FIGS. 1A and 2A.

In a comparison between FIGS. 2A and 2B, FIG. 2B is generally regarded as being better for clinical applications because the additional resolution in FIG. 2A does not convey significantly more information, but the additional noise in FIG. 2A creates texture and structure that is distracting and could potentially lead to a poor diagnosis or, during an interventional procedure, a poor outcome. Accordingly, a greater degree of denoising and smoothing can be beneficial for soft-tissue images.

In contrast, a lesser degree of denoising and smoothing can be beneficial for lung images. In a comparison between FIGS. 1A and 1B, FIG. 1A is generally regarded as being better for clinical applications because the additional resolution in FIG. 1A is significant to being able to distinguish the features of the lungs (e.g., the feature pointed to by the arrow in FIG. 1A), and the additional noise is still relatively small compared to the high-contrast features (i.e., large signal amplitudes) in the lung region.

Thus, FIGS. 1A, 1B, 2A, and 2B illustrate that the degree of denoising can depend on the content/context of an image. That is different regions within the same image can benefit from different degrees of denoising/smoothing.

In contrast to the spatially-varying content-oriented $β_c$ approach described herein, some other approaches use only a spatially-invariant regularization parameter $β_g$, and still other approaches use only a statistical-based spatially-varying regularization parameter $β_s$. For example, in a first approach, the regularization parameter can be a single spatially-invariant value $β_g$, which is determined empirically by users, and the value $β_g$ is applied uniformly (spatially invariant) to the whole image. This spatially-invariant regularization parameter is denoted as $β_g$. This approach as the advantage of being simple, but unlike the methods described herein, this approach can lead to non-uniform noise distribution in the reconstructed image, including within a given organ.

To overcome this non-uniform noise distribution in the reconstructed image, a second approach aims to achieve a uniform noise distribution in the reconstruction field of view by scaling the regularization parameter based on back-projecting a statistical weight in the data. This second approach yields a spatially-varying regularization parameter $β_s$, which is a matrix that has the same dimension as the reconstructed image matrix (i.e., the matrix of volume pixel (voxel) values). The resulting total regularization parameter becomes the product $β_g β_s$. This second approach is illustrated, for example, in U.S. Pat. No. 9,478,049, incorporated herein by reference in its entirety.

In certain implementations, the second approach also uses a normalization process to determine the spatially-varying regularization parameter $β_s$ in order to address the variation of the statistical weight in the axial direction (e.g., due to variations in thickness of a body dimension/radiodensity along the axial direction). These variations can be accounted for, e.g., by normalizing the spatially-varying factor $β_s$ in the axial direction so that the mean $β_s$ within a ROI on each transverse slice is nearly a constant.

In contrast to this second approach, the methods described herein can provide a third term $β_c$, which is a context/content-oriented spatially-varying coefficient regularization parameter, resulting in the total regularization parameter becoming the product $β_g β_s β_c$. Although uniform noise distribution is desirable within a given organ, the methods described herein provide a further improvement by enabling uniform noise distributions within each organ respectively, while also allowing different noise levels for different organs. That is, the methods described herein provide intra-organ uniformity of the noise distribution with inter-organ diversity of the noise distribution.

Without the additional context/content-oriented regularization parameter $β_c$ these other approaches can suffer from several deficiencies. For example, back-projecting the statistical weight to estimate the spatially-varying factor $β_c$ can yield a uniform noise distribution throughout the image, but, as discussed above, in clinical practice a uniform noise distribution across the entire reconstructed image may not be desired.

For example, in detection tasks that involve multiple organs, regions with high-contrast structures (e.g., lungs) permit higher image noise than the regions with low-contrast structures (e.g., abdomen). A regularization parameter β that provides uniform noise distribution throughout the entire image and is optimized for the detection task in the abdomen region might cause significant over-smoothing in the lung and bone regions. Although this could be resolved by running multiple reconstructions using different protocols (e.g., a different $β_g$ values are used to reconstruct respective images optimized for each organ, i.e., lung, body, bone, etc.), running multiple reconstructions can be particularly challenging (i.e., slow and inefficient) in clinical practice where a trauma pan-scan is often needed. Accordingly, in practice, running multiple reconstructions using multiple protocols can disadvantageously lead to complicated workflow, prolonged image processing time, and extra burden on radiologist to read the multiple images.

Figure 3:
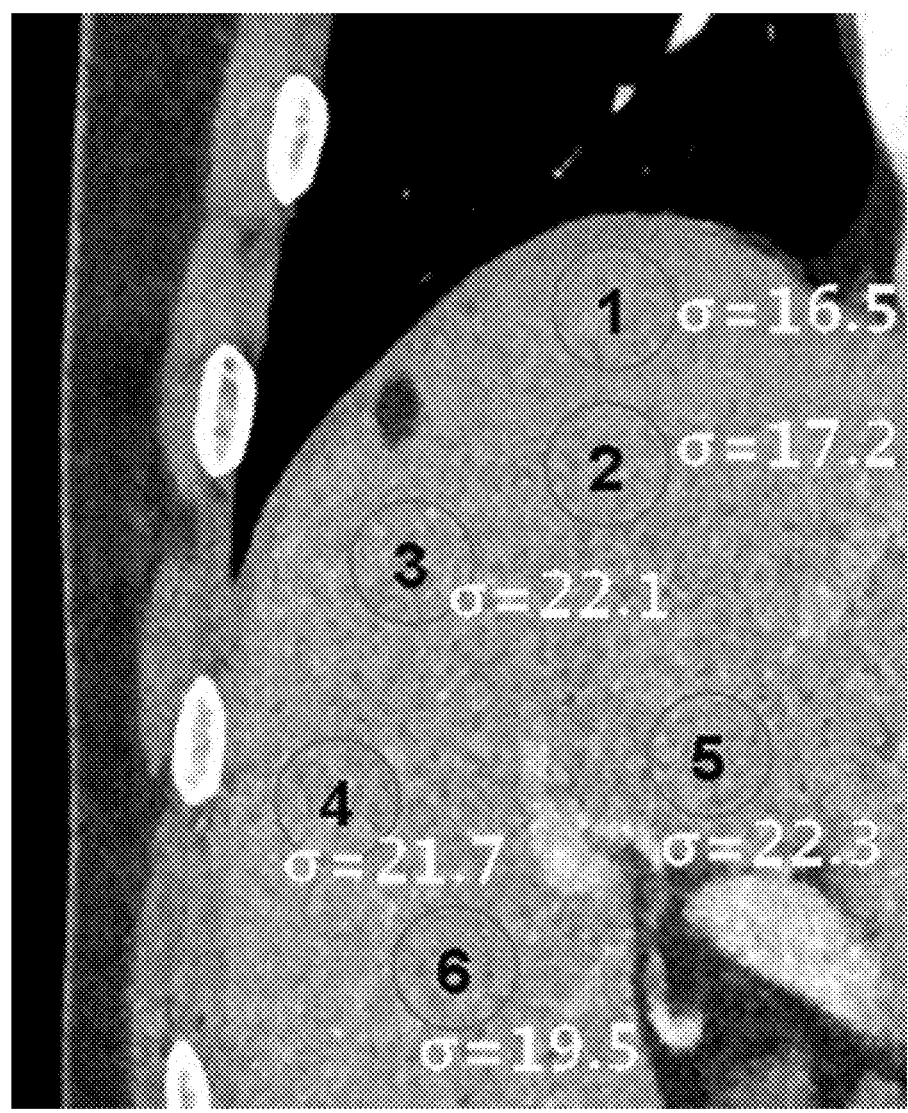
FIG. 3 shows a plot of a reconstructed image using a spatially-varying regularization parameter $\beta$, according to one implementation.
Figure 4:
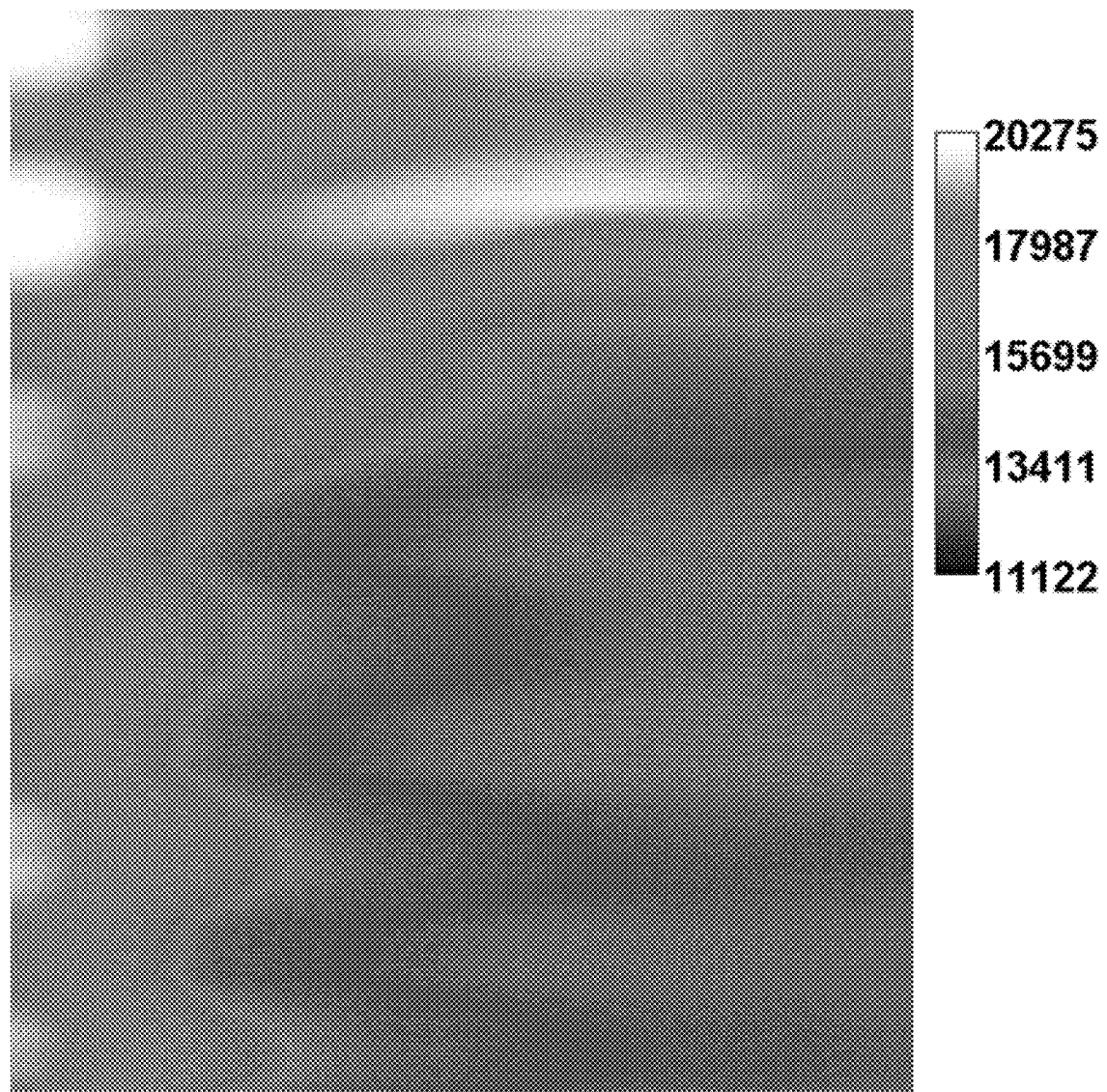
FIG. 4 shows a plot of a spatially-varying regularization parameter $\beta$, according to one implementation.

FIGS. 3 and 4 illustrate another deficiency that is overcome by the methods described herein. This deficiency is found in methods that rely solely on back-projecting the statistical weight to estimate a spatially-varying regularization parameter β without accounting for context/content. FIG. 3 shows a reconstructed image with the local noise (i.e., the standard deviation σ) provided at six points. FIG. 2 shows, for the same region, the values of $β_s$. It is evident that within the liver region the degree of smoothing varies significantly. For example, a higher value of $β_s$ and much more smoothing occurs in the liver dome region, than in the central liver region, resulting in a much lower noise level at points 1 and 2, than at points 3, 4 and 5. This example illustrates that, strong smoothing can gradually propagate from regions with high β into adjacent regions, introducing strong correlation between neighboring voxels. In FIG. 3, for example, the liver dome region (i.e., points 1 and 2) exhibit less noise than rest of the liver (i.e., points 3-6) because the strong smoothing enforced by the large β values in the lungs are smoothed/propagate into the region of liver dome, as shown in FIG. 4.

To remedy the above-noted deficiencies, the method described herein use an iterative reconstruction (IR) algorithm that uses prior knowledge of the anatomical structures being reconstructed to regulate the regularization strength in the reconstruction. Accordingly, this approach can enforce invariant noise distribution within a single organ while allowing variant noise distribution across different organs. That is, the methods described herein provide intra-organ uniformity of the smoothing/noise distribution while allowing inter-organ diversity of the smoothing/noise distribution.

In certain implementations, this prior knowledge can be in the format of an organ map obtained from a previously reconstructed image (e.g., an initial CT image). For example, the previously reconstructed image can be generated and incorporated into a spatially-varying β-map using the following steps. First, generate a preliminary reconstruction. Second, based on the preliminary reconstructed image, employ a classification method to generate an organ-dependent β scaling map. For example, an efficient classification method can use hierarchical piece-wise linear HU-to-β mapping, as discussed below. Third, estimate a spatially-varying β-map that encourages spatially invariant noise distribution within given regions. Fourth, scale this spatially-varying β-map to realize the desired degree of smoothing within each organ using the organ-dependent β scaling map. Fifth, use the scaled β volume (i.e., the total β-map) in the IR algorithm to reconstruct a second/updated image.

In certain implementations, the IR algorithm can be formulated as an unconstrained (or constrained) optimization problem to find the argument p that minimizes the expression $$\underset{p}{\operatorname{argmin}}\{\|Ap - \ell\|_W^2 + \beta U(p)\},$$

wherein l is the projection data representing the logarithm of the X-ray intensity of projection images taken at a series of projection angles and p is a reconstructed image of the X-ray attenuation for voxels/volume pixels (or two-dimensional pixels in a two-dimensional reconstructed image) in an image space. For the system matrix A, each matrix value $a_{ij}$ (i being a row index and j being a column index) represents an overlap between the volume corresponding to voxel $p_j$ and the X-ray trajectories corresponding to projection value $l_i$. The data-fidelity term $\|A_p - l\|_W^2$ is minimized when the forward projection A of the reconstructed image p provides a good approximation to all measured projection images l. Thus, the data fidelity term is directed to solving the system matrix equation Ap=l, which expresses the Radon transform (i.e., projections) of various rays from a source through an object OBJ in the space represented by p to X-ray detectors generating the values of l (e.g., X-ray projections through the three-dimensional object OBJ onto a two-dimensional projection image l).

The notation $\|g\|_W^2$ signifies a weighted inner product of the form $g^T W g$, wherein W is the weight matrix (e.g., expressing a reliability of trustworthiness of the projection data based on a pixel-by-pixel signal-to-noise ratio). In other implementations, the weight matrix W can be replaced by an identity matrix. When the weight matrix W is used in the data fidelity term, the above IR method is referred to as a penalized weighted least squares (PLWS) approach.

In certain implementations, the regularization parameter β is a product of three terms, i.e., $$\beta = \beta_g \beta_s \beta_c \text{ or}$$

$$\beta_j = \beta_g \beta_{s,j} \beta_{c,j}$$

wherein $β_j$ is the $j^{th}$ term of the total β-map β, $β_g$ is the spatially-invariant coefficient, $β_{s,j}$ is the $j^{th}$ term of the statistical-weight dependent spatially-varying coefficient $β_s$, and $β_{c,j}$ is the $j^{th}$ term of the context-oriented spatially-varying coefficient $β_c$.

Figure 5:
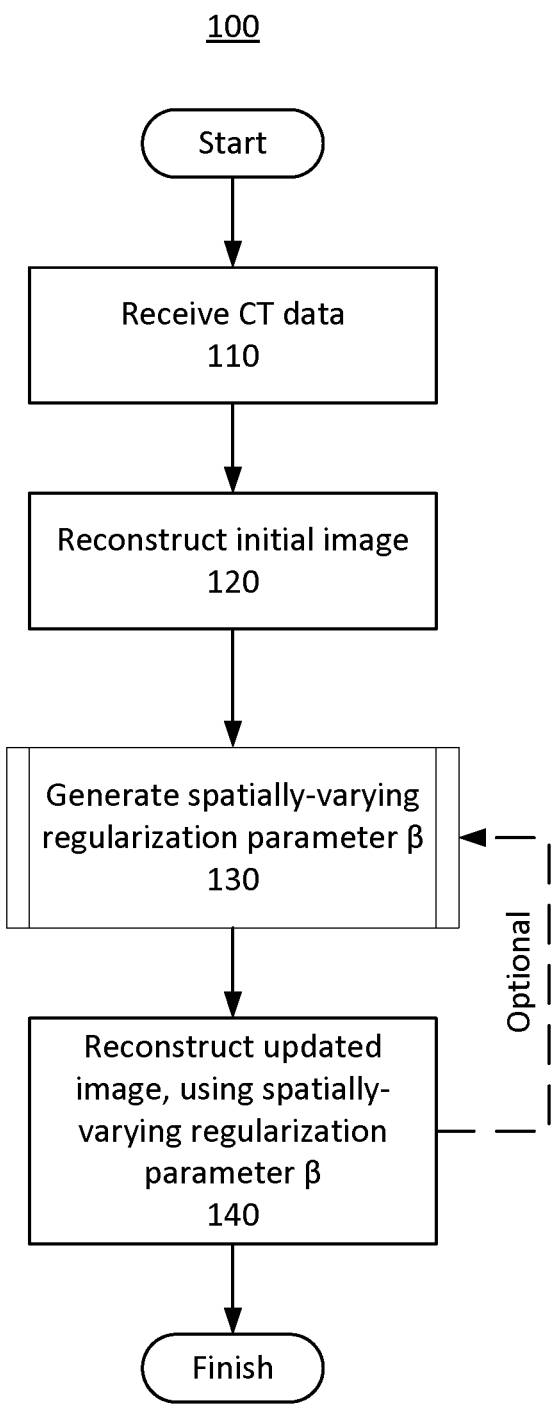
FIG. 5 shows a flow diagram of a method for reconstructing an image using a spatially-varying regularization constant that is based on the content/context of a CT image, according to one implementation.

FIG. 5 shows a flow diagram of a method 100 for generating a spatially-varying total β-map β and reconstructing an image using the total β-map β.

In step 110 of method 100, projection data from a CT scan is obtained.

In step 120 of method 100, an initial CT image is reconstructed from the obtained projection data. This initial CT image can form the prior knowledge of the anatomical structures being reconstructed, which is used to determine the statistical and content/context information used to generate the spatially-varying coefficients/matrices $β_s$ and $β_c$. The initial CT image can be generated using any known reconstruction method, but, in certain implementations, computationally efficient methods, such as filtered backprojection (FBP), can be preferred in order to provide a low-cost image that is sufficient for segmentation/classification of the initial CT image into regions according to organ type or radiodensity.

Figure 7:
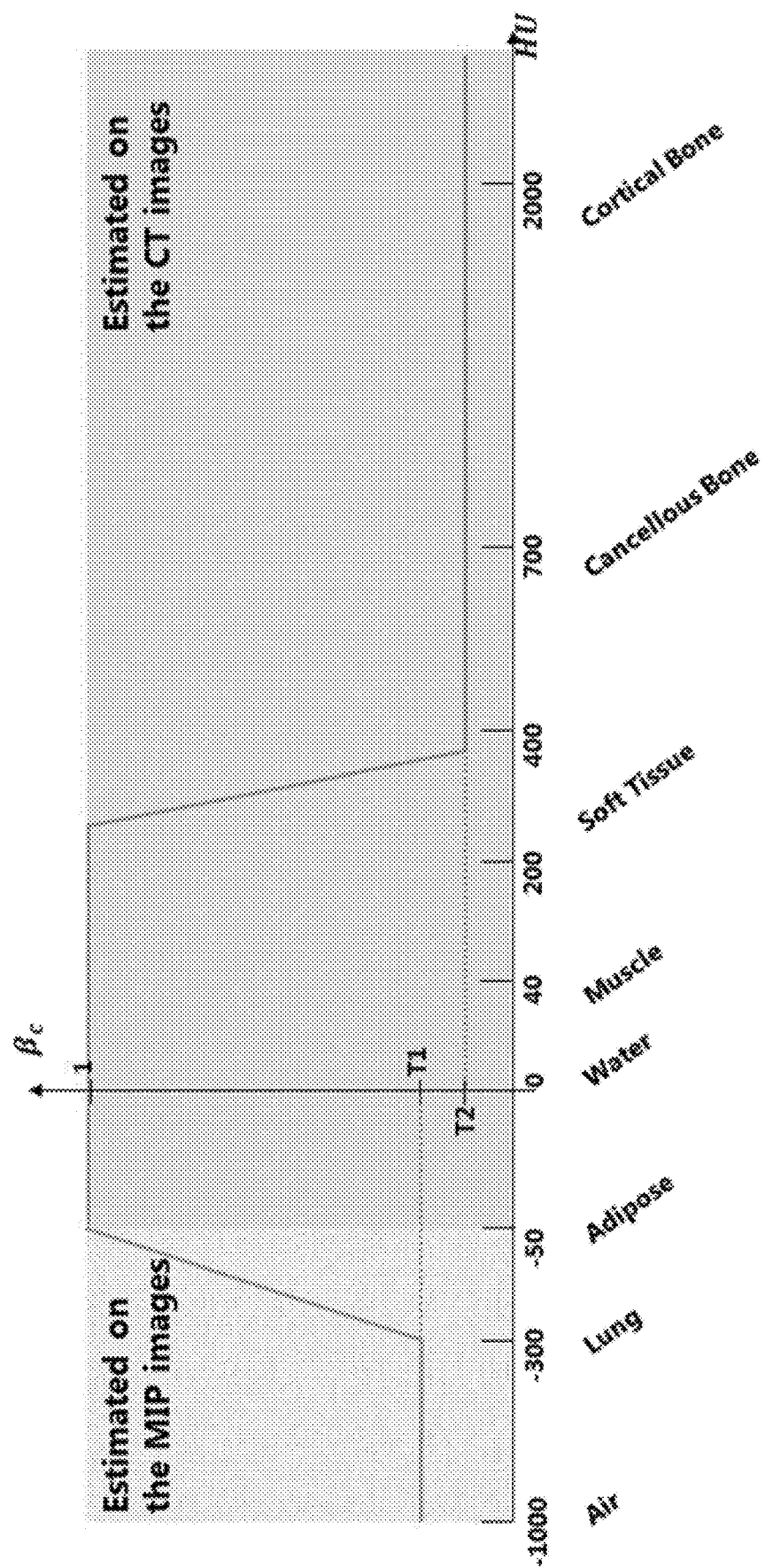
FIG. 7 shows a plot of an HU-to-$\beta$ mapping, according to one implementation.

In process 130 of method 100, the total β-map β is generated in part based on the content/context represented in the initial CT image. The initial CT image can be segmented/classified into organs/regions using any segmentation method. In certain implementations, a threshold and region growing method is used to segment the initial CT image into regions corresponding to different organs. In certain implementations, an anatomical/body atlas and/or pattern recognition processing can be used assign organ labels to respective regions. Further, when the projection data includes spectral information, material decomposition can be performed, and the initial CT image can include two or more material-component images. This material-component information (e.g., bone versus soft tissues) can be used to classify regions in the initial CT image. Further, in certain implementations, the radiodensity information can be used to classify regions in the initial CT image according to organ types. For example, different ranges of radiodensity can be identified on a Hounsfield Units (HU) scale, as shown in FIG. 7 for air, lung, adipose, water, muscle, soft tissue, cancellous bone, and cortical bone. Additionally, any combination of the above-identified methods for segmenting and classifying the initial CT image can be used to determine the content of the initial CT image. As would be understood by a person of ordinary skill in the art, variations and changes can be made to process 130, without departing from the spirit of the invention (e.g., changes can be made to the method of determining the content/context information from the initial CT image and then mapping the content/context information onto the total β-map $\beta_{Total}$).

In step 140 of method 100, an updated CT image is reconstructed using the obtained projection data and the total β-map $\beta_{Total}$. In certain implementations, method 100 can include an optional feedback mechanism in which the updated CT image is fed back from step 140 to process 130. Then, during a second and subsequent iteration, the updated CT image is used in place of the initial image to generate the total β-map $\beta_{Total}$. By using a higher quality image for the total β-map $\beta_{Total}$, a more accurate representation of the content can be obtained and the updated CT image can be improved. The updated CT image can be reconstructed using any IR algorithm that includes a regularization term.

For example, IR algorithms are often formulated as a constrained (unconstrained) optimization problem to find an argument p (i.e., the reconstructed image) that minimize an objective/cost function, wherein the regularization term is formulated as a roughness penalty. In certain implementations, regularization is performed using minimizing a total-variation minimization (TV) regularizer in conjunction with a positivity constraint imposed as a projection on convex sets (POCS). The TV regularizer can be incorporated into the cost function, e.g., $$\underset{p}{\operatorname{argmin}}\{\|Ap - \ell\|_W^2 + \beta\|p\|_{TV}\},$$

wherein $\|p\|_{TV} = \|\nabla_p\|_1$ is the $l_1$-norm of the gradient-magnitude image, which is the isotropic TV semi-norm. The spatial-vector image ∇p represents a discrete approximation to the image gradient. Alternatively, some regularizer can be imposed as constraints. For example, a combination of TV and POCS regularization are imposed as constraints when the optimization problem is framed as $$p^* = \underset{p}{\operatorname{argmin}}\{\|Ap - \ell\|_W^2 \text{ s.t. } \|p\|_{TV} \leq \beta \text{ and } p_j \geq 0.$$

So far, the data fidelity term in the cost function has been for post-log projection data. Alternatively, a pre-log data fidelity term can be used, e.g., when the X-ray flux onto the detectors is low. In the discussion below the symbol y∝exp(−l) is used to represent the pre-log projection data. After preprocessing the X-ray detector counts to account for calibrations and data corrections (e.g., beam-hardening, detector nonlinearities, k escape, pileup, etc.), CT data can, in practice, be modeled by independent random variables following a Poisson distribution with additive Gaussian distribution to account for electronic noise in the measurement. The statistical model of the random variable $Y_i$ measured by the detector element i can be described as $$Y_i \sim \text{Poisson}(\bar{y}_i(p)) + \text{Gaussian}(0, \sigma_e^2)$$

wherein $\sigma_e^2$ denotes the standard deviation of electronic noise. The value $\bar{y}_i(p)$ is the expected pre-log projection data related to the attenuation image p by means of a nonlinear transformation, which is given by $$\bar{y}_i(p) = b_i \exp(-[Ap]_i) + r_i$$

wherein $b_i$ is a calibration factor of the detector element i determined, e.g., during a calibration scan, and $r_i$ is the mean of background measurement (e.g., scattered photons). In pre-log methods, the attenuation image p can be reconstructed, e.g., from the measurement y using a complex likelihood function or from the shifted data $$\hat{Y}_i = [Y_i + \sigma_e^2]_+ \sim \text{Poisson}(\bar{y}_i(p) + \sigma_e^2),$$

using the tractable shifted-Poisson model, wherein $[\bullet]_+$ is a threshold function that sets negative values to zero. For the shifted-Poisson model, the image estimate is obtained by maximizing the log likelihood function of the shifted-Poisson model, which is given by $$p^* = \underset{p \geq 0}{\operatorname{argmax}} \sum_i [\hat{y}_i \log(\bar{y}_i(p) + \sigma_e^2) - (\bar{y}_i(p) + \sigma_e^2)] - \beta U(p),$$

wherein U(p) is a regularizer that represents an image roughness penalty. For example, the regularization term can be determined as the intensity difference between neighboring voxels, which is given by $$U(p) = \sum_j \sum_{k \in N_j} w_{jk} \psi_\delta(p_j - p_k),$$

wherein $\psi_\delta(t)$ is the penalty function, δ is a parameter that controls the smoothness of the penalty function, $w_{jk}$ is the weighting factor related to the distance between voxel j and voxel k in the neighborhood $N_j$. An example of $\psi_\delta(t)$ is the Huber function, which can be expressed as $$\psi_\delta(t) = \begin{cases} \frac{1}{2}t^2, & \delta \geq |t| \\ \delta|t| - \frac{\delta^2}{2}, & \text{otherwise} \end{cases}.$$

In addition to the Huber function, the regularization term U(p) can be a quadratic regularization term, a total variation minimization term, or any other regularization term.

Figure 6:
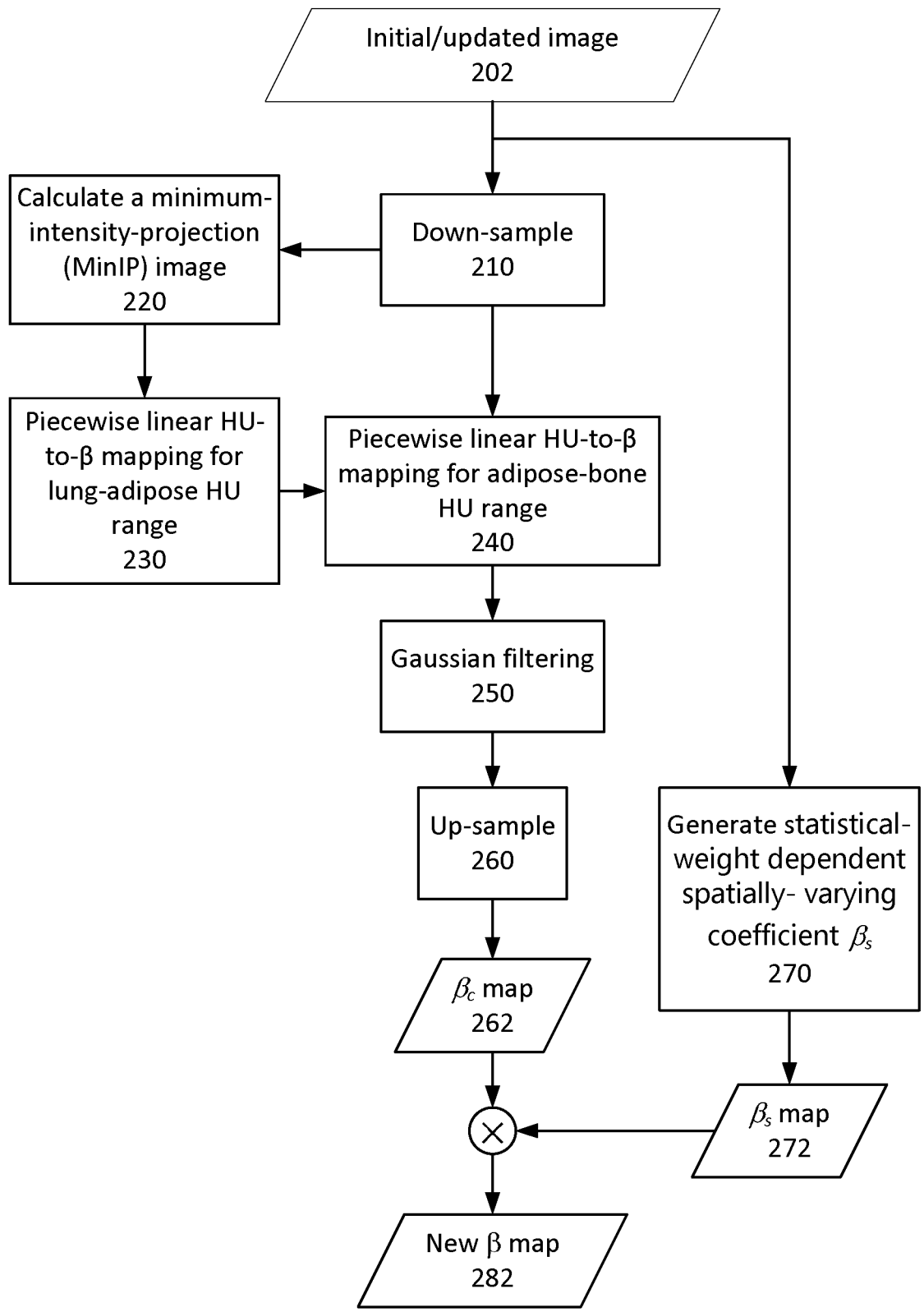
FIG. 6 shows a flow diagram of a process for calculating a spatially-varying regularization constant, according to one implementation.

FIG. 6 shows a flow diagram of a non-limiting implementations of the process 130 for generating a spatially-varying total β-map that includes an organ-dependent scaling $\beta_c$. The organ-dependent regularization parameter $\beta_c$ obtained using the implementation in FIG. 6 treats sub-solid lung nodules regions differently than adipose-water regions. The process starts with the initial/updated image 202.

In certain implementations, the organ-dependent scaling $\beta_c$-map can be constant within a given organ while varying among the organs. In certain implementations, the organ-dependent scaling $\beta_c$-map is a function of the HU values within certain organs/regions. For example, FIG. 7 shows a non-limiting example in which the value of the scaling $\beta_c$-map is constant for regions and HU values in the air-lung range (i.e., between −1000 HU and −300 HU), and is linearly related to HU values of the initial/updated CT image 202 in the lung-adipose range (i.e., between −300 HU and −50 HU).

To determine $\beta_c$, the initial image 202 is used to classify the organs. As discussed above, the classification can be achieved using a segmentation method, e.g., in some implementations, any segmentation method can work. However, for certain implementations, a non-iterative segmentation method with minimal parameter tuning can produce better, more efficient performance.

For images that include a lung region, one challenge, which is encountered during the classifying step, is how to differentiate sub-solid lung nodules from adipose-water tissues. Often, stronger smoothing is desired on adipose and water regions while less smoothing is desired on the sub-solid lung nodules due to their important clinical implications. However, differentiating sub-solid lung nodules from adipose-water can be challenging because sub-solid lung nodules have similar radiodensity as adipose and water, and, therefore, sub-solid lung nodules and adipose-water regions can prove challenging to differentiate solely based on the HU values in the initial CT image 202. This challenge is addressed through the use of a minimum intensity projection (MIP) image, which is generated in step 220 shown in FIG. 6.

In step 210, the initial/updated image 202 is down-sampled. Often low spatial resolution is sufficient for the total β-map β, and process 130 can be performed faster by down-sampling the images to decrease their size. However, steps 210 and 260 are not required and can be omitted, in certain implementations.

In steps 220, 230, and 240 a hierarchical piece-wise linear HU-to-β mapping is used to differentiate sub-solid lung nodules regions from adipose-water regions, and then assign different $\beta_c$ values to these different regions.

In step 220, the MIP image is generated from the down-sampled CT image. For example, FIG. 9A shows an example of a CT image, and FIG. 9B shows an example of the MIP image is generated from the CT image in FIG. 9A.

To generate the MIP image at step 220, the down-sampled CT image is processed to eliminate most of the sub-solid lung nodules. For example, sub-solid nodules vary substantially along an axial direction. This variation along the axial direction is illustrated in the example of an initial CT image shown in FIG. 9A. The cross hairs indicate a sub-solid nodule, and, in the coronal and sagittal views, the indicated sub-solid nodule exhibits substantial variation in radiodensity along the axial direction (i.e., the vertical axis). Thus, in the MIP image, the sub-solid nodules are essentially eliminated by replacing the pixel value in a given axial slice by the smallest value in the stack of 20 neighboring slices. That is, for each voxel f(x, y, z) in the preliminary reconstructed CT image, the values of the voxel f(x, y, z) is replaced by the minimum intensity value in a f(x, y, z−10) to f(x, y, z+10) sub-stack (20 neighboring slices in the z direction, i.e., the axial direction).

Figure 9A:
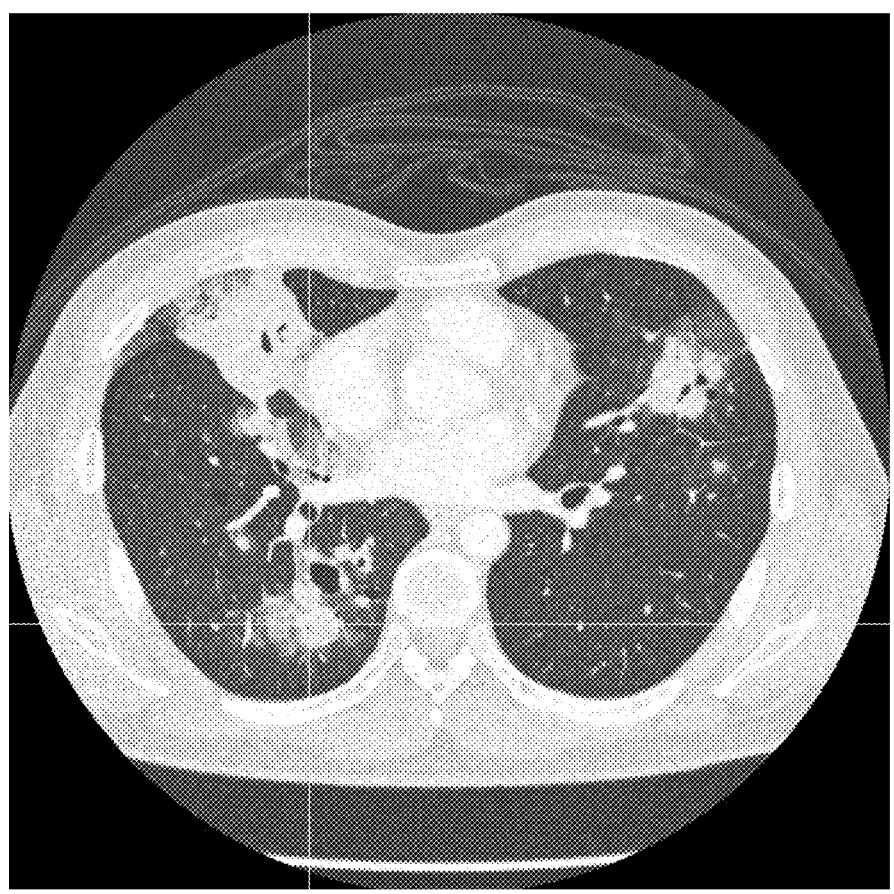
FIG. 9A shows a transverse view, a coronal view, and a sagittal view of a computed tomography (CT) image, according to one implementation.
Figure 9A:
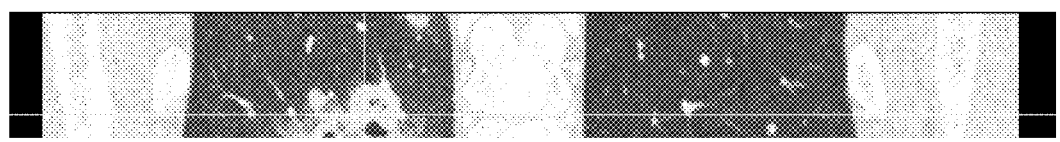
Figure 9A:
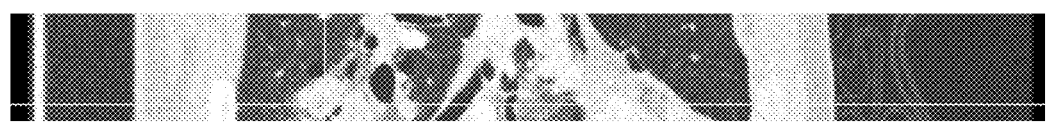
Figure 9B:
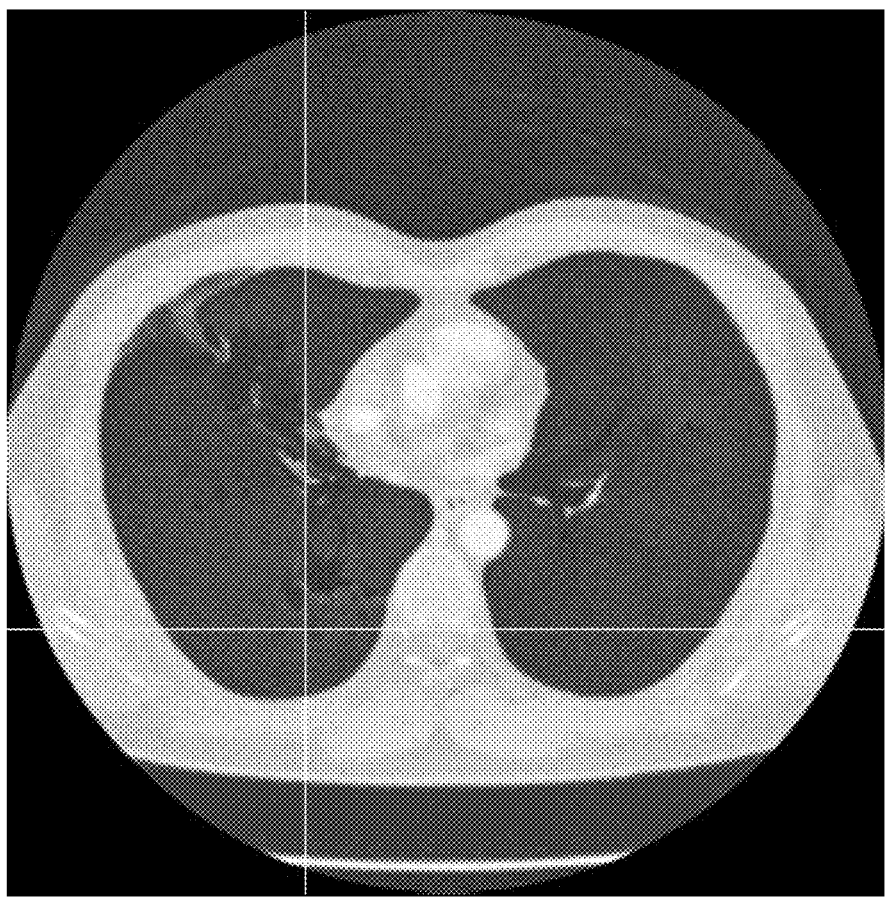
FIG. 9B shows a transverse view, a coronal view, and a sagittal view of a minimum intensity projection (MIP) mapping of the CT image in FIG. 9A, according to one implementation.
Figure 9B:
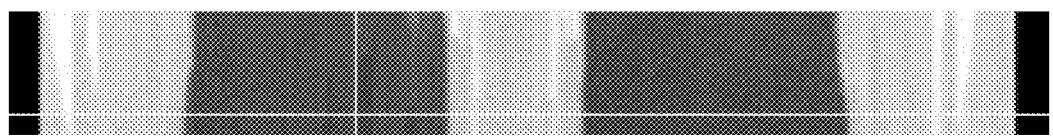
Figure 9B:
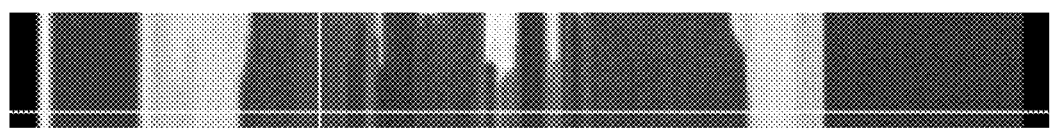

An example of this mapping is shown in the MIP image in FIG. 9B, corresponding to the initial CT image shown in FIG. 9A. It can be seen that the sub-solid lung nodules have been effectively eliminated in the MIP image. Further, in FIG. 9B, the shape of the heart is also changed in the MIP image. However, for the organs with higher than adipose HU value, their corresponding value on the β-map will be estimated based on the CT image in the second level of the mapping.

In step 230, the MIP image is used to determine which pixels have values within a first range of the HU scale from −1000 HU to −50 HU, corresponding to air, lung, and up to adipose on the scale shown in FIG. 7. For pixels $f_j$ of the down-sampled CT image falling within the first range, a first HU-to-β mapping is performed using HU values pixels $f_j^{MIP}$ of the MIP image to values for the spatially-varying regularization parameter $\beta_c$, i.e., $$\beta_c = \begin{cases} T_1, & -1000 < f_j^{MIP} < -300 \text{ and } f_j < -50 \\ \frac{f_j^{MIP} - (-300)}{-50 - (-300)} \times (1 - T_1) + T_1, & -300 \leq f_j^{MIP} \leq -50 \text{ and } f_j < -50 \end{cases}.$$

In step 240, for all remaining pixels (i.e., pixels $f_j$ for which the HU value in the down-sampled CT image exceeds −50 HU), a second HU-to-β mapping is performed using pixel values $f_j$ of the down-sampled CT image, i.e., $$\beta_c = \begin{cases} 1 & -50 < f_j < 300 \\ \frac{fj - 350}{300 - 350} \times (1 - T_2) + T_2, & 300 \leq fj \leq 350 \\ T_2, & 350 < f_j \end{cases}.$$

This bifurcation into the first and second mappings that respectively use the MIP pixels $f_j^{MIP}$ and the down-sampled CT pixels $f_j$ is advantageous for images that include lung regions. For example, stronger smoothing is desired on adipose/water dominated regions while less smoothing is desired on the sub-solid lung nodules, e.g., due to their important clinical implications. The sub-solid lung nodules tend to be small, and, therefore, are essentially eliminated in the MIP image. Thus, they are assigned a value of $T_1$ for $\beta_c$, even though the HU values for the sub-solid lung nodules are often in the adipose-to-muscle range.

In step 250, smoothing (e.g., Gaussian filtering) can be applied to the $\beta_c$-map generated at steps 230 and 240. For example, this smoothing can help to mitigate discontinuities between the first and second mappings, resulting from the use of two different images, i.e., the MIP image and the down-sampled CT image.

In step 260, the $\beta_c$-map 262 is up-sampled to be the same dimensions as the initial/updated image 202.

In step 270, the statistical-weight-dependent spatially-varying $\beta_s$-map is generated. For example, the $\beta_s$-map 272 can be determined based on criteria for maintaining uniform statistical distribution. The $\beta_c$-map 262 and the $\beta_s$-map 272 are then multiplied pixel-by-pixel to generate a total β-map 282 $\beta_{Total}$, which, in certain implementations, can also include a constant multiplicative factor $\beta_g$.

Figure 8A:
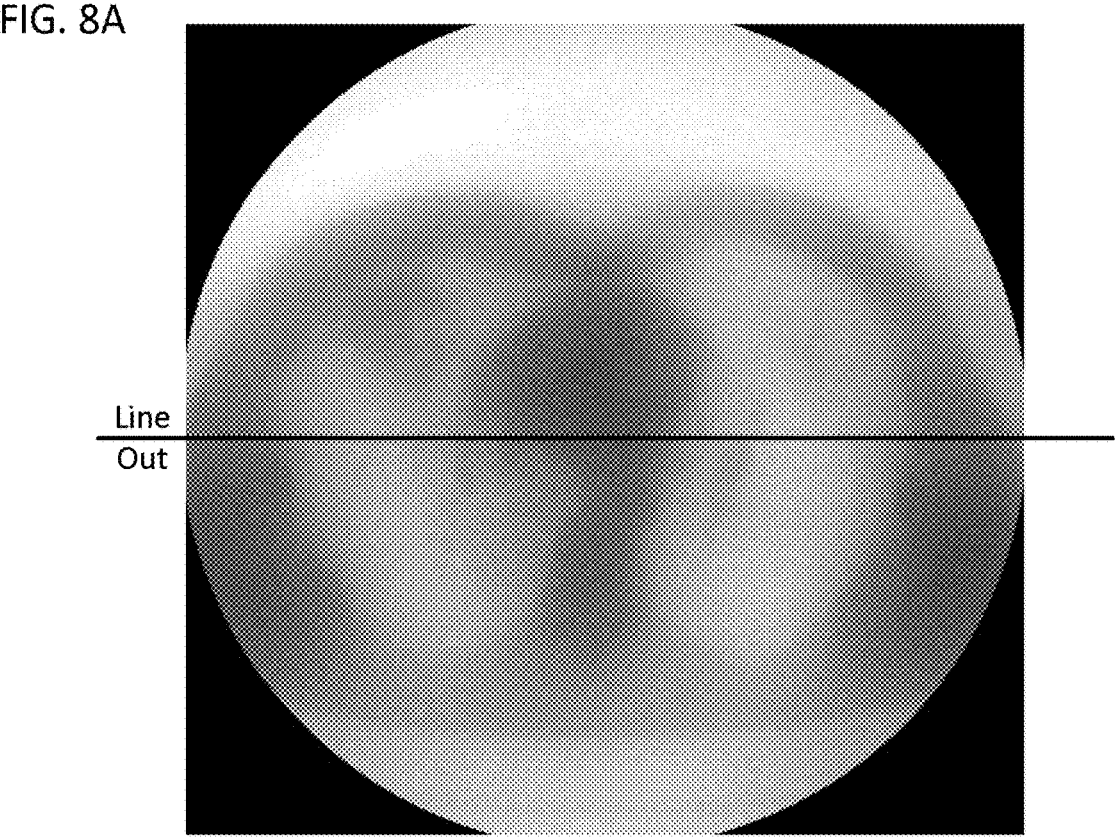
FIG. 8A shows a $\beta$ mapping for a statistically constant reconstructed image, according to one implementation.
Figure 8B:
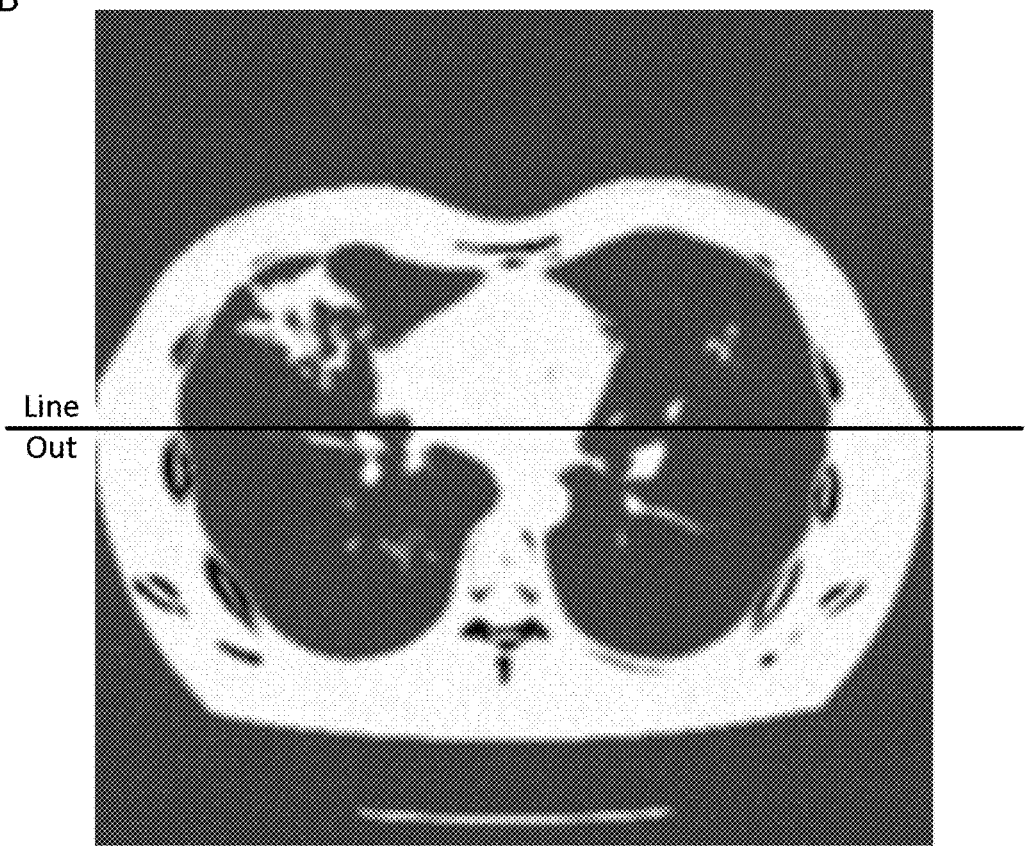
FIG. 8B shows $\beta$ mapping for an organ-dependent reconstructed image, according to one implementation.
Figure 8C:
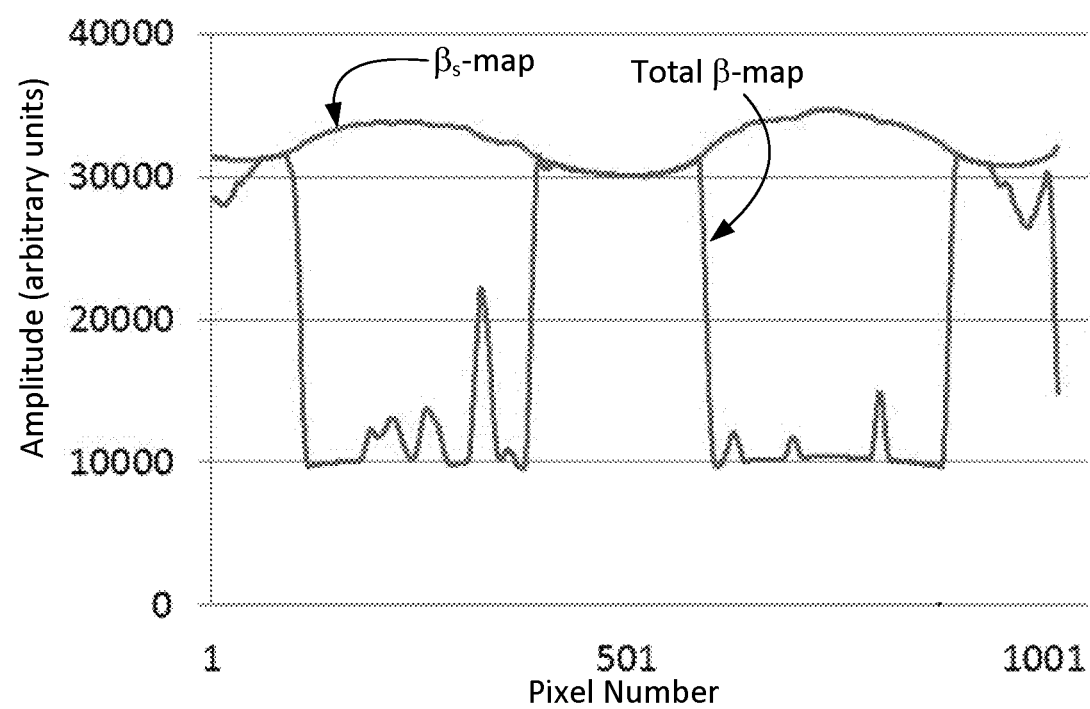
FIG. 8C shows a plot comparing lineouts for the $\beta$ mappings in FIGS. 8A and 8B, according to one implementation.

FIGS. 8A and 8B show images of the $\beta_s$-map 272 and the total β-map 282 (i.e., $\beta_c \times \beta_s$). FIG. 8C shows a lineout for the $\beta_s$-map 272 and the total β-map 282. For HU values between −50 HU and 300 HU the $\beta_s$-map 272 and the total β-map 282 are the same (i.e., between −50 HU and 300 HU $\beta_c$=1 and $\beta_{Total}=\beta_c \times \beta_s$ reduces to $\beta_{Total}=\beta_s$).

Figure 10A:
FIG. 10A shows a first part of a reconstructed image generated using a low degree of smoothing (i.e., $\beta$=9), the image is plotted using WL=−600 HU and WW=1600 HU, according to one implementation.
Figure 10B:
FIG. 10B shows a second part of the reconstructed image generated using a low degree of smoothing (i.e., $\beta$=9), the image is plotted using WL=−600 HU and WW=1600 HU, according to one implementation.
Figure 10C:
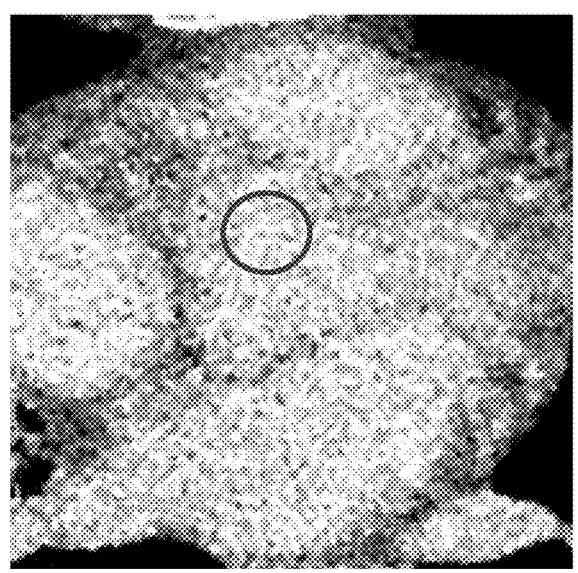
FIG. 10C shows a third part a reconstructed image generated using a low degree of smoothing (i.e., $\beta$=9), the image is plotted using WL=40 HU and WW=400 HU, according to one implementation.

FIGS. 10A, 10B, and 10C show respective regions within a low-smoothing reconstructed image that is generated using $\beta_s$ without using $\beta_c$ (i.e., $\beta_{Total}=\beta_g \beta_s$, wherein $\beta_g$=9). The standard deviation σ within the circle region in FIG. 10C is σ=55.

Figure 11A:
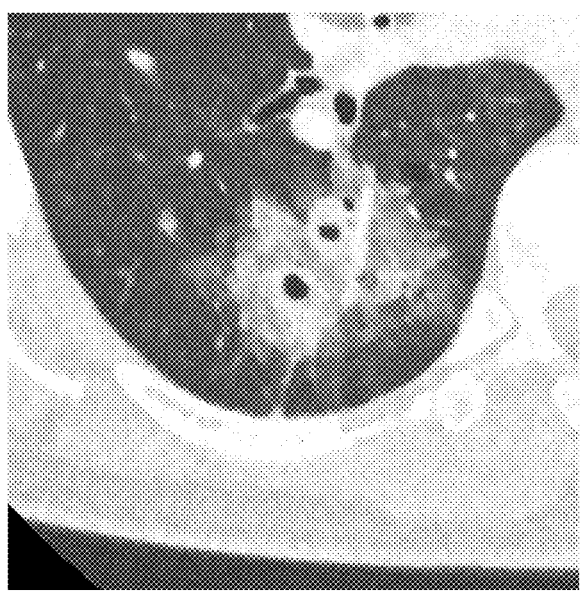
FIG. 11A shows the first part of a reconstructed image generated using a high degree of smoothing (i.e., $\beta$=26), the image is plotted using WL=−600 HU and WW=1600 HU, according to one implementation.
Figure 11B:
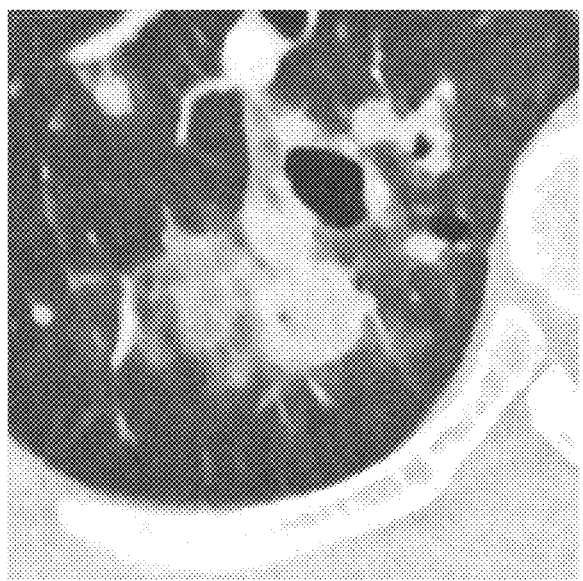
FIG. 11B shows the second part of the reconstructed image generated using a high degree of smoothing (i.e., β=26), the image is plotted using WL=−600 HU and WW=1600 HU, according to one implementation.
Figure 11C:
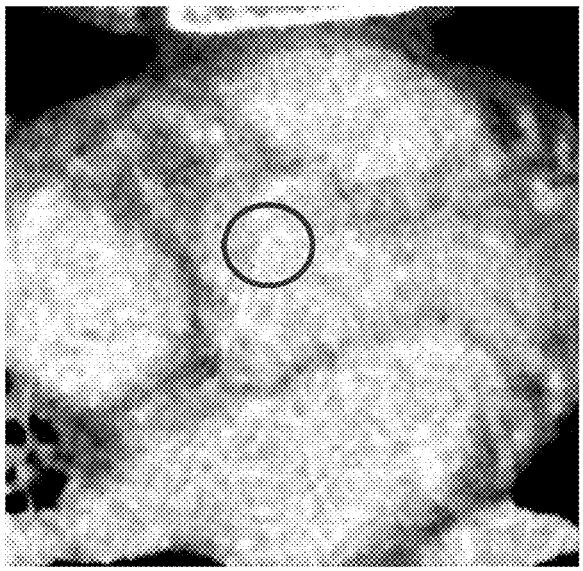
FIG. 11C shows the third part of a reconstructed image generated using a high degree of smoothing (i.e., β=26), the image is plotted using WL=40 HU and WW=400 HU, according to one implementation.

FIGS. 11A, 11B, and 11C show respective regions within a high-smoothing reconstructed image that is generated using $\beta_c$ without using $\beta_s$ (i.e., $\beta_{Total}=\beta_g\beta_s$, wherein $\beta_g=26$). The standard deviation σ within the circle region in FIG. 11C is σ=26.

Figure 12A:
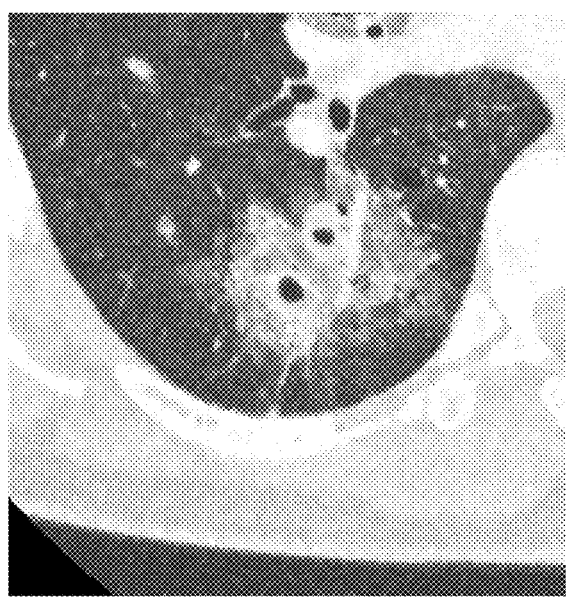
FIG. 12A shows the first part of a reconstructed image generated using a different degrees of smoothing based on the context/content of the image, the image is plotted using WL=−600 HU and WW=1600 HU, according to one implementation.
Figure 12B:
FIG. 12B shows the second part of the reconstructed image generated using a high degrees of smoothing based on the context/content of the image, the image is plotted using WL=−600 HU and WW=1600 HU, according to one implementation.
Figure 12C:
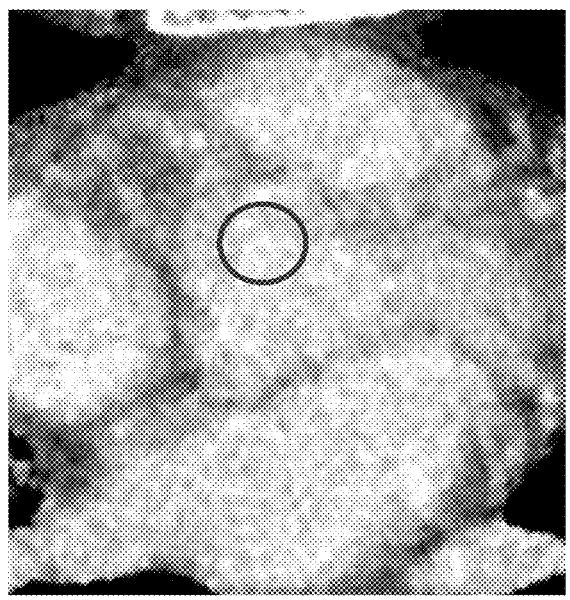
FIG. 12C shows the third part of a reconstructed image generated using a high degrees of smoothing based on the context/content of the image, the image is plotted using WL=40 HU and WW=400 HU, according to one implementation.

FIGS. 12A, 12B, and 12C show respective regions within a high-smoothing reconstructed image that is generated using both $\beta_s$ and $\beta_c$ (i.e., $\beta_{Total}=\beta_g\beta_s\beta_c$, wherein $\beta_g=26$). The standard deviation σ within the circle region in FIG. 12C is σ=25.

Without $\beta_c$, a tradeoff between noise and resolution is clearly evident. The low-smoothing images in FIGS. 10A and 10B exhibit good contrast, but the high-smoothing images in FIGS. 11A and 11B exhibit poor contrast. On the other hand, the low-smoothing image in FIG. 10C exhibits poor signal-to-noise ratio (SNR), whereas the high-smoothing image in FIG. 10C exhibits good SNR.

In the images reconstructed with $\beta_c$, FIGS. 12A and 12B exhibit good contrast, while FIG. 12C simultaneously exhibits good SNR because the value of $\beta_{Total}$ is reduced in the lung regions to ensure low smoothing and good resolution, while the value of $\beta_{Total}$ is maintained near its maximum level in the adipose-to-soft tissue region to ensure high smoothing and a reduced noise level that improves the SNR.

Figure 13A:
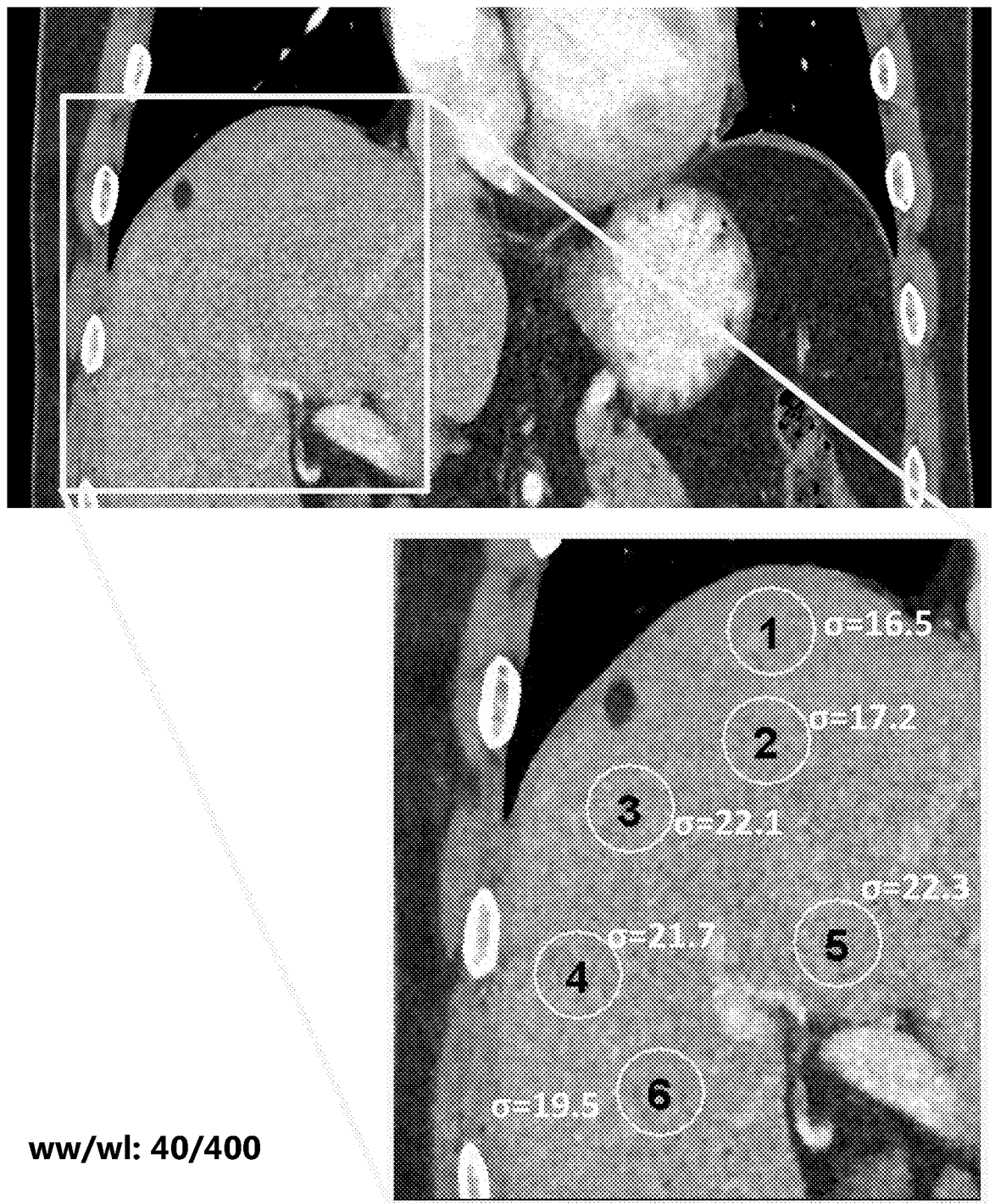
FIG. 13A shows statistical variations within a liver region of a reconstructed image generated using a related method, the image is plotted using WL=40 HU and WW=400 HU according to one implementation.
Figure 13B:
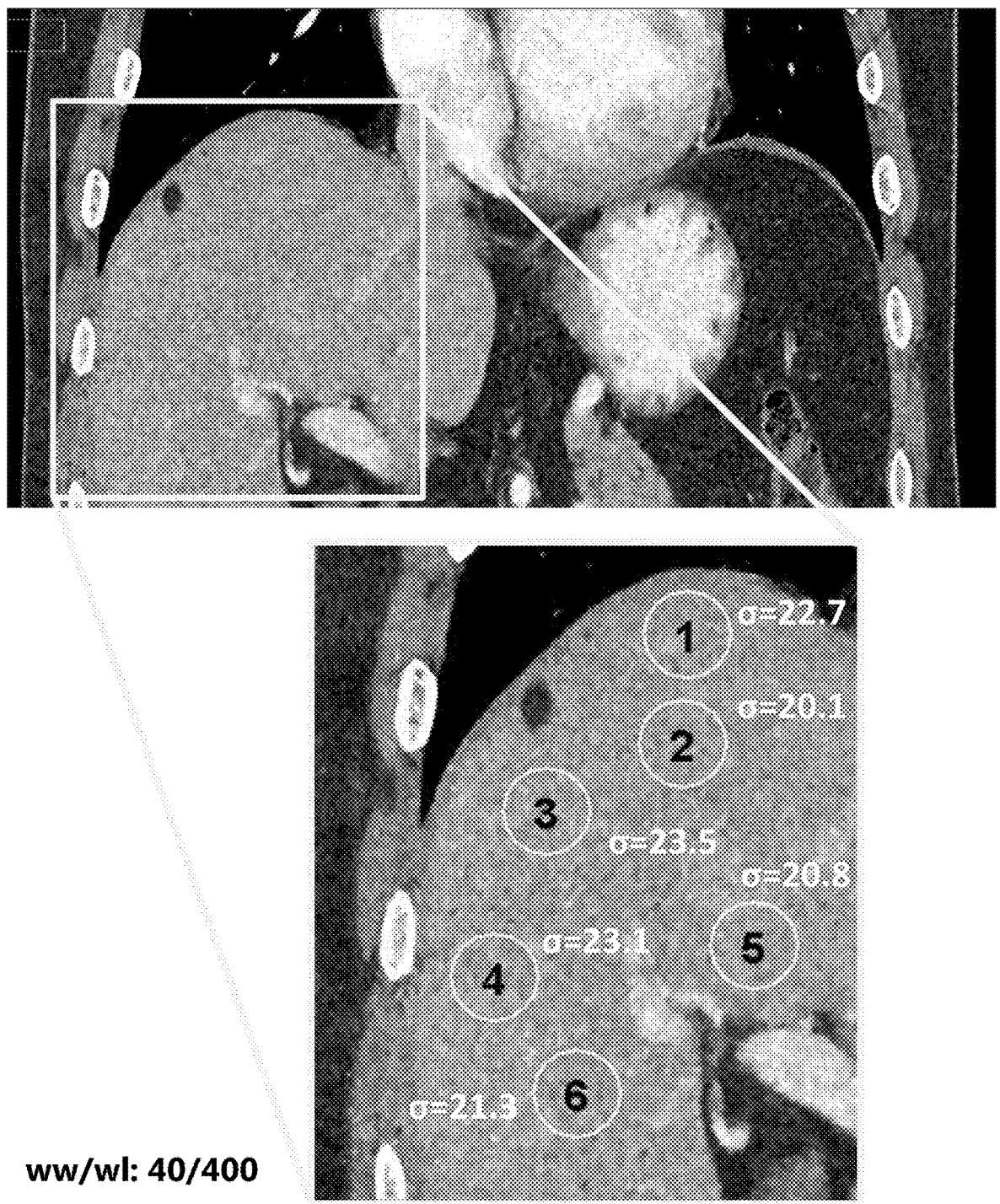
FIG. 13B shows statistical variations within a liver region of a reconstructed image generated using a context/content-oriented method described herein, the image is plotted using WL=40 HU and WW=400 HU according to one implementation.
Figure 14A:
FIG. 14A shows artifacts in a reconstructed image generated using a related method, the image is plotted using WL=40 HU and WW=400 HU according to one implementation.
Figure 14B:
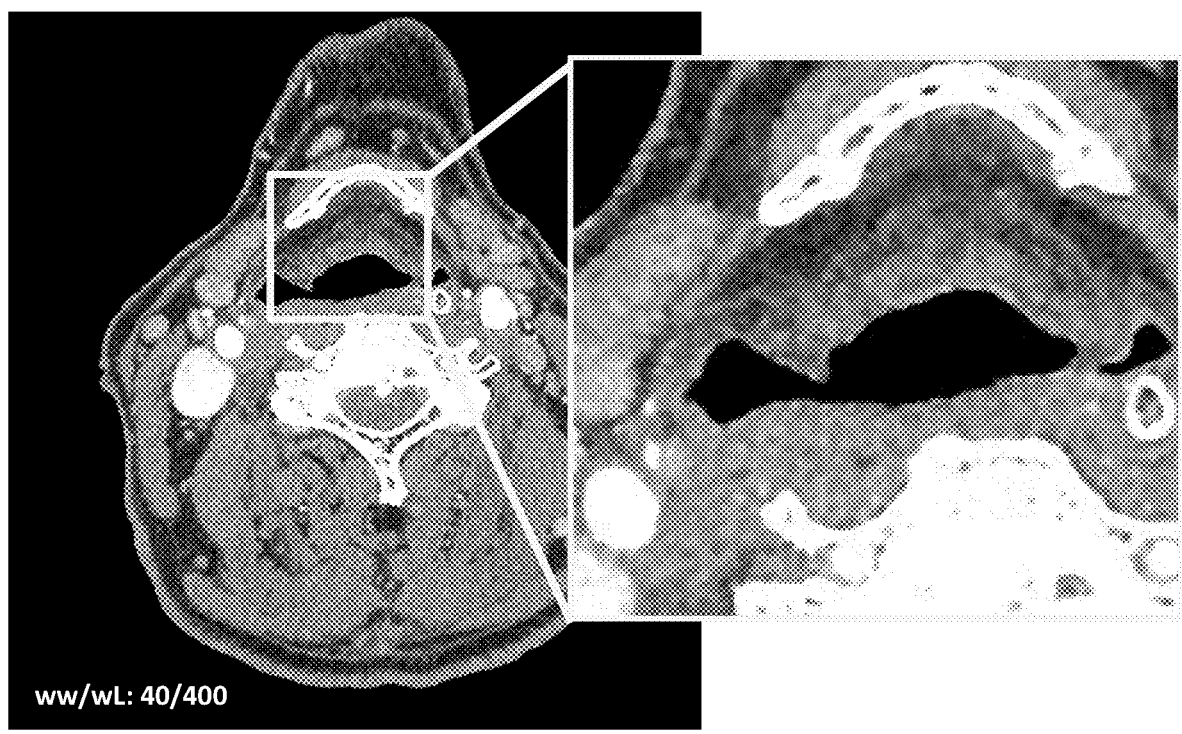
FIG. 14B shows an absence of artifacts in a reconstructed image generated using a context/content-oriented method described herein, the image is plotted using WL=40 HU and WW=400 HU according to one implementation.

FIGS. 13A and 13B show images reconstructed using only both $\beta_s$ and both $\beta_s$ and $\beta_c$, respectively. In FIG. 13A, the standard deviation is lower near the liver dome because, as discussed above with reference to FIGS. 3 and 4, the stronger smoothing in the neighboring voxels of the lung region bleeds/propagates into the liver dome regions. In contrast, the method of content-oriented determination of $\beta_{Total}$ does not suffer from these defects because different region/organs are treated separately. Thus, in FIG. 13B, the standard deviation is essentially uniform throughout the liver.

The use of a context/content-oriented spatially-varying regularization parameter $\beta_c$ in image reconstruction has several advantages over image reconstruction without a $\beta_c$. Unlike other methods that only encourage uniform noise distribution in the whole image, the methods described herein can uniquely generate organ-dependent signal to noise. For example, higher resolution can be provided in the lung regions, and low noise can be provided in the soft tissue regions, thereby achieving better results in clinical practice. Further, the methods described herein prevent the propagation of strong smoothing from the regions with large β into the adjacent regions with small β. Thus, unlike other methods (see, e.g., FIGS. 3 and 13A), the methods described herein can provide a uniform noise distribution within each of the respective organs/segmented regions. Moreover, for trauma pan-scan application, only a single protocol/reconstruction is required with the methods described herein, rather than separate protocol/reconstruction that is respectively optimized for a corresponding organ/tissue type. By achieving optimal results for multiple organs using only a single protocol/reconstruction, the clinical workflow can be significantly improved, and the number of images to be read can be reduced, leading to increased efficiency and patient throughput.

Figure 15:
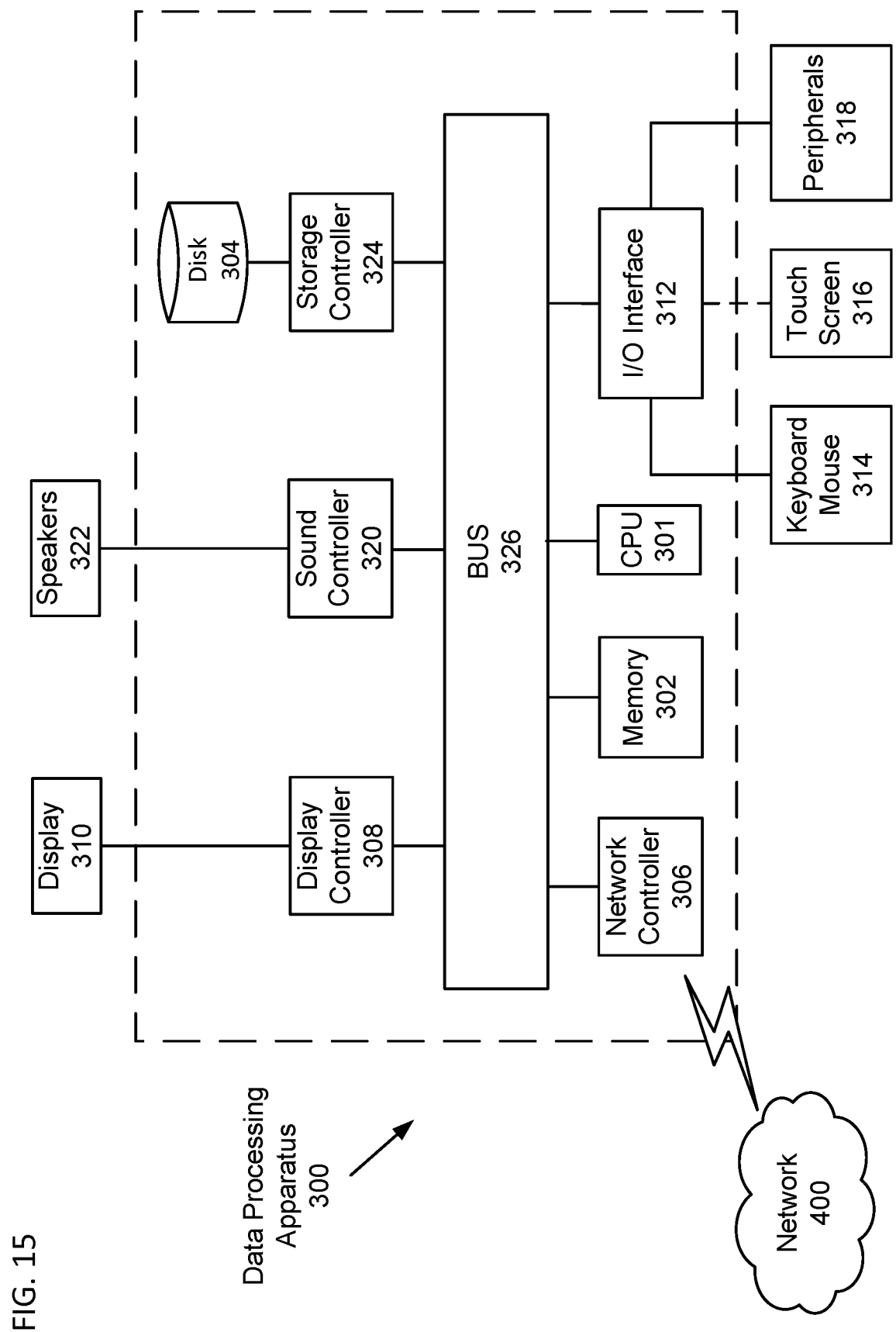
FIG. 15 shows a diagram of a data-processing apparatus for performing the methods described herein, according to one implementation.

Next, a hardware description, according to exemplary embodiments, is described with reference to FIG. 15 for a data-processing apparatus 300 for processing the CT projection data and by performing method 100 and the various processes herein. In FIG. 15, the data-processing apparatus 300 for processing CTP data includes a CPU 301 which performs the processes described above, including method 100, the processes described herein, and variations as would be known to a person of ordinary skill in the art. The process data and instructions may be stored in memory 302. These processes and instructions may also be stored on a storage medium disk 304 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the data-processing apparatus 300 communicates, such as a server or computer.

Further, the claimed advancements may be provided as a utility application, background daemon, or component of an operating system, or combination thereof, executing in conjunction with CPU 301 and an operating system such as Microsoft Windows 7, UNIX, Solaris, LINUX, Apple MAC-OS and other systems known to those skilled in the art.

CPU 301 may be a Xeon or Core processor from Intel of America or an Opteron processor from AMD of America, or may be other processor types that would be recognized by one of ordinary skill in the art. Alternatively, the CPU 301 may be implemented using a GPU processor such as a Tegra processor from Nvidia Corporation and an operating system, such as Multi-OS. Moreover, the CPU 301 may be implemented on an FPGA, ASIC, PLD or using discrete logic circuits, as one of ordinary skill in the art would recognize. Further, CPU 301 may be implemented as multiple processors cooperatively working in parallel to perform the instructions of the inventive processes described above.

The data-processing apparatus 300 in FIG. 15 also includes a network controller 306, such as an Intel Ethernet PRO network interface card from Intel Corporation of America, for interfacing with network 400. As can be appreciated, the network 400 can be a public network, such as the Internet, or a private network such as an LAN or WAN network, or any combination thereof and can also include PSTN or ISDN sub-networks. The network 400 can also be wired, such as an Ethernet network, or can be wireless such as a cellular network including EDGE, 3G and 4G wireless cellular systems. The wireless network can also be WiFi, Bluetooth, or any other wireless form of communication that is known.

The data-processing apparatus 300 further includes a display controller 308, such as a NVIDIA GeForce GTX or Quadro graphics adaptor from NVIDIA Corporation of America for interfacing with display 310, such as a Hewlett Packard HPL2445w LCD monitor. A general purpose I/O interface 312 interfaces with a keyboard and/or mouse 314 as well as a touch screen panel 316 on or separate from display 310. General purpose I/O interface also connects to a variety of peripherals 318 including printers and scanners, such as an OfficeJet or DeskJet from Hewlett Packard.

A sound controller 320 is also provided in the parallel scalar-multiplication apparatus, such as Sound Blaster X-Fi Titanium from Creative, to interface with speakers/microphone 322 thereby providing sounds and/or music.

The general purpose storage controller 324 connects the storage medium disk 304 with communication bus 326, which may be an ISA, EISA, VESA, PCI, or similar, for interconnecting all of the components of the Parallel scalar-multiplication apparatus. A description of the general features and functionality of the display 310, keyboard and/or mouse 314, as well as the display controller 308, storage controller 324, network controller 306, sound controller 320, and general purpose I/O interface 312 is omitted herein for brevity as these features are known.

Figure 16:
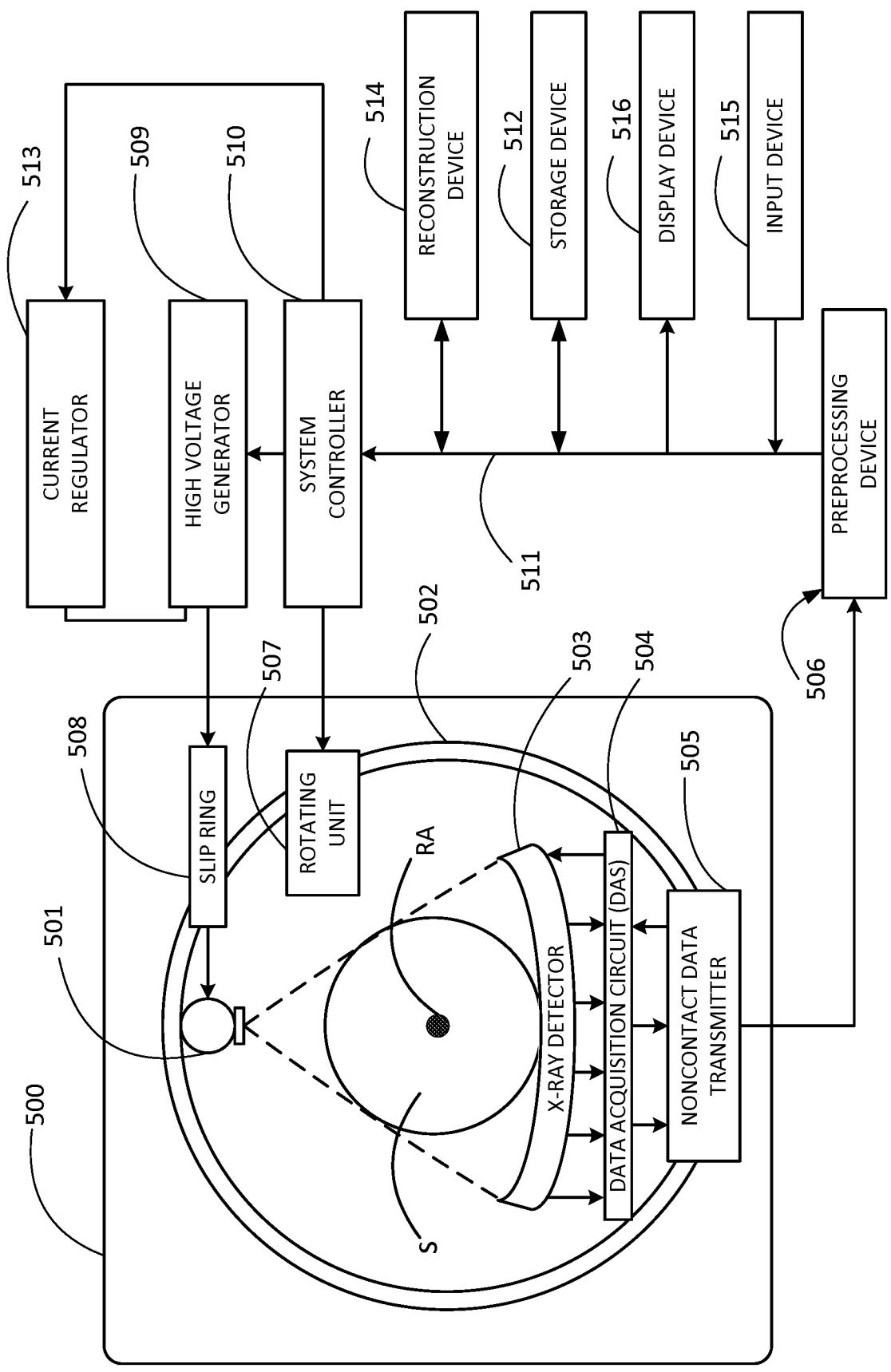
FIG. 16 shows a schematic of an implementation of a CT scanner.

FIG. 16 illustrates an implementation of the radiography gantry included in a CT apparatus or scanner. As shown in FIG. 16, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA. A rotating unit 507 rotates the annular frame 502 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal. The X-ray detector 503 and the DAS 504 are configured to handle a predetermined total number of projections per rotation (TPPR).

The above-described data is sent to a preprocessing device 506, which is housed in a console outside the radiography gantry 500 through a non-contact data transmitter 505. The preprocessing device 506 performs certain corrections, such as sensitivity correction on the raw data. A memory 512 stores the resultant data, which is also called projection data at a stage immediately before reconstruction processing. The memory 512 is connected to a system controller 510 through a data/control bus 511, together with a reconstruction device 514, input device 515, and display 516. The system controller 510 controls a current regulator 513 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 501 and the X-ray detector 503 are diametrically mounted on the annular frame 502 and are rotated around the object OBJ as the annular frame 502 is rotated about the rotation axis RA. In the fourth-generation geometry system, the detectors are fixedly placed around the patient and an X-ray tube rotates around the patient. In an alternative embodiment, the radiography gantry 500 has multiple detectors arranged on the annular frame 502, which is supported by a C-arm and a stand.

The memory 512 can store the measurement value representative of the irradiance of the X-rays at the X-ray detector unit 503. Further, the memory 512 can store a dedicated program for executing method 100.

The reconstruction device 514 can reconstruct CT images and can execute post processing of the reconstructed CT images, including method 100 described herein. Further, reconstruction device 514 can execute pre-reconstruction processing image processing such as volume rendering processing and image difference processing as needed.

The pre-reconstruction processing of the projection data performed by the preprocessing device 506 can include correcting for detector calibrations, detector nonlinearities, and polar effects, for example.

Post-reconstruction processing performed by the reconstruction device 514 can include filtering and smoothing the image, volume rendering processing, and image difference processing as needed. Further, the post-reconstruction processing can include jagged-edge removal and resolution enhancement using method 100 and/or 200. The image reconstruction process can be performed using known methods, including, e.g., filtered-backprojection, iterative reconstruction, algebraic reconstruction techniques, ordered subsets, and acceleration techniques. The reconstruction device 514 can use the memory to store, e.g., projection data, reconstructed images, calibration data and parameters, and computer programs.

The reconstruction device 514 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 512 can be non-volatile, such as ROM, EPROM, EEPROM or FLASH memory. The memory 512 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 514 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 516. The display 516 can be an LCD display, CRT display, plasma display, OLED, LED or any other display known in the art.

The memory 512 can be a hard disk drive, CD-ROM drive, DVD drive, FLASH drive, RAM, ROM or any other electronic storage known in the art.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
   circuitry configured to
      obtain projection data representing an intensity of X-ray radiation for a series of projection images of attenuation through an object, the series of projection images being acquired at respective projection angles,
      reconstruct a first computed tomography (CT) image from the projection data,
      classify the first CT image into a plurality of regions corresponding to respective organs and/or tissue types,
      determine respective first regularization parameters corresponding to the plurality of regions, and
      reconstruct, using the projection data and the first regularization parameters, a second CT image using a regularizer that is scaled by the respective first regularization parameters in corresponding regions of the plurality of regions,
   wherein the circuitry is further configured to
   classify the first CT image by generating a minimum intensity projection (MIP) image based on a minimum value in an axial direction of a stack of slices of the first CT image, the stack of slices of the first CT image being taken in axial planes, and
   determine the first regularization parameters using the first CT image to determine the first regularization parameters of pixels of the first CT image within a first range of radiodensity, and using the MIP image to determine the first regularization parameters of pixels of the first CT image within a second range of radiodensity, a radiodensity in the first range of radiodensity being greater than a radiodensity in the second range of radiodensity.

2. An apparatus, comprising:
   circuitry configured to
      obtain projection data representing an intensity of X-ray radiation for a series of projection images of attenuation through an object, the series of projection images being acquired at respective projection angles,
      reconstruct a first computed tomography (CT) image from the projection data,
      classify the first CT image into a plurality of regions corresponding to respective organs and/or tissue types,
      determine respective first regularization parameters corresponding to the plurality of regions, and
      reconstruct, using the projection data and the first regularization parameters, a second CT image using a regularizer that is scaled by the respective first regularization parameters in corresponding regions of the plurality of regions,
   wherein the circuitry is further configured to
   determine the first regularization parameters using a piece-wise linear mapping from values of radiodensity to values of the first regularization parameters, the piece-wise linear mapping being applied to pixels of the first CT image that have a radiodensity within a first range of radiodensities,
   generate a minimum intensity projection (MIP) image based on a minimum value in an axial direction of a stack of slices of the first CT image, the stack of slices of the first CT image being taken in axial planes, and,
   for pixels of the first image having a radiodensity outside of the first range of radiodensities, apply the piece-wise linear mapping to the MIP image to determine the first regularization parameters.

3. An apparatus, comprising:
   circuitry configured to
      obtain projection data representing an intensity of X-ray radiation for a series of projection images of attenuation through an object, the series of projection images being acquired at respective projection angles,
      reconstruct a first computed tomography (CT) image from the projection data,
      classify the first CT image into a plurality of regions corresponding to respective organs and/or tissue types,
      determine respective first regularization parameters corresponding to the plurality of regions, and
      reconstruct, using the projection data and the first regularization parameters, a second CT image using a regularizer that is scaled by the respective first regularization parameters in corresponding regions of the plurality of regions,
   wherein the circuitry is further configured to determine the first regularization parameters, wherein the first regularization parameters, when used to reconstruct the second CT image, cause greater smoothing in a soft tissue region of the plurality of regions than in a lung region of the plurality of regions.

4. A method, comprising:
   obtaining projection data representing an intensity of X-ray radiation for a series of projection images of attenuation through an object, the series of projection images being acquired at respective projection angles,
   reconstructing a first computed tomography (CT) image from the projection data;
   classifying the first CT image into a plurality of regions corresponding to respective organs and/or tissue types,
   determining respective first regularization parameters corresponding to the plurality of regions, and
   reconstructing, using the projection data and the first regularization parameters, a second CT image using a regularizer that is scaled by the respective first regularization parameters in corresponding regions of the plurality of regions,
   wherein the determining of the first regularization parameters is performed using a piece-wise linear mapping from values of radiodensity to values of the first regularization parameters, the piece-wise linear mapping being applied to pixels of the first image that have a radiodensity within a first range of radiodensities,
   the method further comprising:

generating a minimum intensity projection (MIP) image based on a minimum value in an axial direction of a stack of slices of the first CT image, the stack of slices of the first CT image being taken in axial planes, and for pixels of the first image having a radiodensity outside of the first range of radiodensities, applying the piecewise linear mapping to the MIP image to determine the first regularization parameters.

5. A method, comprising:

obtaining projection data representing an intensity of X-ray radiation for a series of projection images of attenuation through an object, the series of projection images being acquired at respective projection angles;

reconstructing a first computed tomography (CT) image from the projection data;

classifying the first CT image into a plurality of regions corresponding to respective organs and/or tissue types;

determining respective first regularization parameters corresponding to the plurality of regions; and reconstructing, using the projection data and the first regularization parameters, a second CT image using a regularizer that is scaled by the respective first regularization parameters in corresponding regions of the plurality of regions;

wherein the first regularization parameters, when used to reconstruct the second CT image, cause greater smoothing in a soft tissue region of the plurality of regions than in a lung region of the plurality of regions.

6. A non-transitory computer-readable storage medium including executable instruction, wherein the instructions, when executed by circuitry, cause the circuitry to perform the method according to claim 4.

* * * * *